(12) United States Patent
Hori et al.

(10) Patent No.: US 11,306,295 B2
(45) Date of Patent: Apr. 19, 2022

(54) HEAT-RESISTANT LUCIFERASE

(71) Applicants: TOYO B-NET CO., LTD., Tokyo (JP); TOYO INK SC HOLDINGS CO., LTD., Tokyo (JP)

(72) Inventors: Ayumi Hori, Ibaraki (JP); Yutaka Yamagishi, Tokyo (JP)

(73) Assignees: TOYO B-NET CO., LTD., Tokyo (JP); TOYO INK SC HOLDINGS CO., LTD., Tokyo (JP)

( * ) Notice: Subject to any disclaimer, the term of this patent is extended or adjusted under 35 U.S.C. 154(b) by 168 days.

(21) Appl. No.: 16/494,311

(22) PCT Filed: Mar. 14, 2018

(86) PCT No.: PCT/JP2018/010060
§ 371 (c)(1),
(2) Date: Sep. 16, 2019

(87) PCT Pub. No.: WO2018/168958
PCT Pub. Date: Sep. 20, 2018

(65) Prior Publication Data
US 2020/0017840 A1    Jan. 16, 2020

(30) Foreign Application Priority Data
Mar. 17, 2017    (JP) .............................. JP2017-052502

(51) Int. Cl.
*C12N 9/02*      (2006.01)
*C12N 15/70*    (2006.01)
*C12Q 1/66*     (2006.01)
*G01N 21/76*   (2006.01)

(52) U.S. Cl.
CPC ........... *C12N 9/0069* (2013.01); *C12N 15/70* (2013.01); *C12Q 1/66* (2013.01); *C12Y 113/12007* (2013.01); *G01N 21/763* (2013.01)

(58) Field of Classification Search
CPC ........ C12N 9/0069; C12N 15/70; C12N 5/10; C12Q 1/66; C12Y 113/12007; G01N 21/763
See application file for complete search history.

(56) References Cited

U.S. PATENT DOCUMENTS

2014/0080199 A1* 3/2014 Ogo .................. C07K 14/43563
435/189

FOREIGN PATENT DOCUMENTS

| JP | 3048466    | 6/2000  |
| JP | 3681911    | 8/2005  |
| JP | 3844082    | 11/2006 |
| JP | 2010088440 | 4/2010  |
| JP | 2011200146 | 10/2011 |
| JP | 2012205584 | 10/2012 |
| JP | 5090304    | 12/2012 |
| JP | 5185479    | 4/2013  |
| JP | 5951325    | 7/2016  |

OTHER PUBLICATIONS

Siloto RMP et al. Site saturation mutagenesis: Methods and Applications in Protein Engineering. 2012. Biocatalysis and Agricultural Biotechnology. 1:181-189 (Year: 2012).*
Singh RK et al. Protein Engineering Approaches in the Post-Genomic Era. 2017. Current Protein and Peptide Science. 18:1-11 (Year: 2017).*
Zhang M et al. Propagated Perturbations from a Peripheral Mutation Show Interactions Supporting WW Domain Thermostability. 2018. Structure. 26:1474-1485. (Year: 2018).*
"International Preliminary Report on Patentability (Form PCT/IB/373) of PCT/ JP2018/010060," dated Sep. 26, 2019, with English translation thereof, pp. 1-14.
G.H.Erica Law et al., "Mutagenesis of solvent-exposed amino acids in Photinus pyralis luciferase improves thermostability and pH-tolerance," Biochem J., vol. 397, No. 2, Jul. 15, 2006, pp. 305-312.
"International Search Report (Form PCT/ISA/210)" of PCT/JP2018/010060, dated Jun. 19, 2018, with English translation thereof, pp. 1-4.

* cited by examiner

*Primary Examiner* — Paul J Holland
(74) *Attorney, Agent, or Firm* — JCIPRNET

(57) ABSTRACT

A new thermostable luciferase of the following mutant luciferase (a) or (b): (a) a mutant of a wild-type luciferase comprising the amino acid sequence of SEQ ID NO: 1, wherein phenylalanine at position 292 and/or phenylalanine at position 294 in the amino acid sequence of SEQ ID NO: 1 is substituted with another amino acid; or (b) a mutant of a luciferase having 93% or more homology with the amino acid sequence of SEQ ID NO: 1, wherein in the amino acid sequence of the mutant, the amino acid at a site corresponding to position 292 and/or position 294 in the amino acid sequence of SEQ ID NO: 1 is substituted with another amino acid.

5 Claims, 3 Drawing Sheets
Specification includes a Sequence Listing.

SEQUENCE LISTING

<160> NUMBER OF SEQ ID NOS: 34

<210> SEQ ID NO 1
<211> LENGTH: 550
<212> TYPE: PRT
<213> ORGANISM: Photinus pyralis

<400> SEQUENCE: 1

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

```
Tyr Ala Leu Val Pro Gly Thr Ile Ala Phe Thr Asp Ala His Ile Glu
        35                  40                  45
Val Asn Ile Thr Tyr Ala Glu Tyr Phe Glu Met Ser Val Arg Leu Ala
 50                  55                  60
Glu Ala Met Lys Arg Tyr Gly Leu Asn Thr Asn His Arg Ile Val Val
 65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
                100                 105                 110
Glu Leu Leu Asn Ser Met Asn Ile Ser Gln Pro Thr Val Val Phe Val
                115                 120                 125
Ser Lys Lys Gly Leu Gln Lys Ile Leu Asn Val Gln Lys Lys Leu Pro
        130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
                180                 185                 190
Ala Leu Ile Met Asn Ser Ser Gly Ser Thr Gly Leu Pro Lys Gly Val
                195                 200                 205
Ala Leu Pro His Arg Thr Ala Cys Val Arg Phe Ser His Ala Arg Asp
        210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
                260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
        290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
                355                 360                 365
Phe Glu Ala Lys Val Val Asp Leu Asp Thr Gly Lys Thr Leu Gly Val
        370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
                420                 425                 430
Phe Ile Val Asp Arg Leu Lys Ser Leu Ile Lys Tyr Lys Gly Tyr Gln
        435                 440                 445
```

```
Val Ala Pro Ala Glu Leu Glu Ser Ile Leu Leu Gln His Pro Asn Ile
        450                 455                 460

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
        530                 535                 540

Gly Gly Lys Ser Lys Leu
545                 550

<210> SEQ ID NO 2
<211> LENGTH: 1653
<212> TYPE: DNA
<213> ORGANISM: Photinus pyralis

<400> SEQUENCE: 2
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caatcacag aatcgtcgta     240 tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tgtgacaaa acaattgcac tgataatgaa ttcctctgga     600
tctactgggt tacctaaggg tgtggccctt ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780 cgagtcgtct taatgtatag atttgaagaa gagctgtttt tacgatccct tcaggattac     840
aaaattcaaa gtgcgttgct agtaccaacc ctattttcat tcttcgccaa aagcactctg     900
attgacaaat acgatttatc taatttacac gaaattgctt ctgggggcgc acctctttcg     960
aaagaagtcg ggaagcggt tgcaaaacgc ttccatcttc cagggatacg acaaggatat    1020
gggctcactg agactacatc agctattctg attacacccg agggggatga taaaccgggc    1080
gcggtcggta agttgttcc atttttgaa gcgaaggttg tggatctgga taccgggaaa    1140
acgctgggcg ttaatcagag aggcgaatta tgtgtcagag acctatgat tatgtccggt    1200 tatgtaaaca atccggaagc gaccaacgcc ttgattgaca aggatggatg gctacattct    1260
ggagacatag cttactggga cgaagacgaa cacttcttca gttgaccg cttgaagtct    1320 ttaattaaat acaaaggata tcaggtggcc cccgctgaat ggaatcgat attgttacaa    1380 caccccaaca tcttcgacgc gggcgtgca ggtcttcccg acgatgacgc cggtgaactt    1440
cccgccgccg ttgttgtttt ggagcacgga aagacgatga cggaaaaaga gatcgtggat    1500
```

```
tacgtcgcca gtcaagtaac aaccgcgaaa aagttgcgcg gaggagttgt gtttgtggac    1560
gaagtaccga aggtcttac cggaaaactc gacgcaagaa aaatcagaga gatcctcata     1620
aaggccaaga agggcggaaa gtccaaattg taa                                 1653
```

<210> SEQ ID NO 3
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 3

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Leu Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335
```

```
Arg Gln Gly Tyr Gly Leu Thr Glu Thr Thr Ser Ala Ile Leu Ile Thr
                340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Lys Thr Leu Gly Val
        370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ser Lys Leu
545                 550

<210> SEQ ID NO 4
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 4
atggaagacg ccaaaaacat aaagaaaggc ccggcgccat tctatcctct agaggatgga    60
accgctggag agcaactgca taaggctatg aagagatacg ccctggttcc tggaacaatt   120
gcttttacag atgcacatat cgaggtgaac atcacgtacg cggaatactt cgaaatgtcc   180
gttcggttgg cagaagctat gaaacgatat gggctgaata caaatcacag aatcgtcgta   240
tgcagtgaaa actctcttca attctttatg ccggtgttgg gcgcgttatt tatcggagtt   300
gcagttgcgc ccgcgaacga catttataat gaacgtgaat tgctcaacag tatgaacatt   360
tcgcagccta ccgtagtgtt tgtttccaaa aaggggttgc aaaaaatttt gaacgtgcaa   420
aaaaaattac caataatcca gaaaattatt atcatggatt ctaaaacgga ttaccaggga   480
tttcagtcga tgtacacgtt cgtcacatct catctacctc ccggttttaa tgaatacgat   540
tttgtaccag agtcctttga tcgtgacaaa acaattgcac tgataatgaa ttcctctgga   600
tctactgggt tacctaaggg tgtggccctt ccgcatagaa ctgcctgcgt cagattctcg   660
catgccagag atcctatttt tggcaatcaa atcattccgg atactgcgat tttaagtgtt   720
gttccattcc atcacggttt tggaatgttt actacactcg atatttgat atgtggattt   780 cgagtcgtct taatgtatag atttgaagaa gagctgtttt tacgatccct tcaggattac   840
```

```
aaaattcaaa gtgcgttgct agtaccaacc ctattgtcat tcttcgccaa aagcactctg    900
attgacaaat acgatttatc taatttacac gaaattgctt ctgggggcgc acctctttcg    960
aaagaagtcg gggaagcggt tgcaaaacgc ttccatcttc cagggatacg acaaggatat   1020
gggctcactg agactacatc agctattctg attacacccg agggggatga taaaccgggc   1080
gcggtcggta agttgttcc attttttgaa gcgaaggttg tggatctgga taccgggaaa    1140
acgctgggcg ttaatcagag aggcgaatta tgtgtcagag acctatgat tatgtccggt    1200 tatgtaaaca atccggaagc gaccaacgcc ttgattgaca aggatggatg ctacattct    1260 ggagacatag cttactggga cgaagacgaa cacttcttca tagttgaccg cttgaagtct   1320
ttaattaaat acaaaggata tcaggtggcc cccgctgaat tggaatcgat attgttacaa   1380
caccccaaca tcttcgacgc gggcgtggca ggtcttcccg acgatgacgc cggtgaactt   1440
cccgccgccg ttgttgtttt ggagcacgga agacgatga cggaaaaaga gatcgtggat    1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gtccaaattg taa                                1653
```

<210> SEQ ID NO 5
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 5

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205
```

```
Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Leu Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 6
<211> LENGTH: 1653
<212> TYPE: DNA
<213> ORGANISM: Artificial Sequence
<220> FEATURE:
<223> OTHER INFORMATION: Mutant firefly luciferase
```

<400> SEQUENCE: 6

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780
cgagtcgtct taatgtatag atttgaagaa gagctgtttt tacgatccct tcaggattac     840
aaaattcaaa gtgcgttgct agtaccaacc ctatttcat tgttcgccaa agcactctg      900
attgacaaat acgatttatc taatttacac gaaattgctt ctgggggcgc acctctttcg     960
aaagaagtcg gggaagcggt tgcaaaacgc ttccatcttc cagggatacg acaaggatat    1020
gggctcactg agactacatc agctattctg attacacccg aggggatga taaaccgggc    1080
gcggtcggta agttgttcc atttttgaa gcgaaggttg tggatctgga taccgggaaa     1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca gttgaccg cttgaagtct     1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                 1653
```

<210> SEQ ID NO 7
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 7

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45
```

```
Val Asn Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                     85                  90                  95

Phe Ile Gly Val Ala Val Ala Pro Ala Asn Asp Ile Tyr Asn Glu Arg
                100                 105                 110

Glu Leu Leu Asn Ser Met Asn Ile Ser Gln Pro Thr Val Val Phe Val
                115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
                195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
                290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
                340                 345                 350

Pro Arg Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
                370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
450                 455                 460
```

Phe Asp Ala Gly Val Ala Gly Leu Pro Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
        530                 535                 540

Gly Gly Lys Ser Lys Leu
545                 550

<210> SEQ ID NO 8
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 8
atggaagacg ccaaaaacat aaagaaaggc ccggcgccat tctatcctct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg cgcgttatt tatcggagtt     300 gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttt tacgatccct tcaggattac    840
aaaattcaaa gtgcgttgct agtaccaacc ctatttttcat tcttcgccaa agcactctg    900 attgacaaat acgatttatc taatttacac gaaattgctt ctggggcgc acctctttcg    960 aaagaagtcg ggaagcggt tgcaaaacgc ttccatcttc cagggatacg acaaggatat   1020
gggctcactg agactacatc agctattctg attacacccc gtggggatga taaaccgggc   1080
gcggtcggta agttgttcc atttttgaa gcgaaggttg tggatctgga taccgggaaa    1140
acgctgggcg ttaatcagag aggcgaatta tgtgtcagag acctatgat tatgtccggt    1200 tatgtaaaca atccggaagc gaccaacgcc ttgattgaca aggatggatg ctacattct    1260 ggagacatag cttactggga cgaagacgaa cacttcttca gttgaccg cttgaagtct    1320 ttaattaaat acaaaggata tcaggtggcc cccgctgaat tggaatcgat attgttacaa   1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560

```
gaagtaccga aaggtcttac cggaaaactc gacgcaagaa aaatcagaga gatcctcata    1620
aaggccaaga agggcggaaa gtccaaattg taa                                 1653
```

<210> SEQ ID NO 9
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 9

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335
```

```
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
        370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Arg Asp Ala Gly Val Ala Gly Leu Pro Asp Asp Ala Gly Glu Leu
465                 470                 475                 480
Pro Ala Ala Val Val Val Leu Glu His Gly Lys Thr Met Thr Glu Lys
            485                 490                 495
Glu Ile Val Asp Tyr Val Ala Ser Gln Val Thr Thr Ala Lys Lys Leu
        500                 505                 510
Arg Gly Gly Val Val Phe Val Asp Glu Val Pro Lys Gly Leu Thr Gly
    515                 520                 525
Lys Leu Asp Ala Arg Lys Ile Arg Glu Ile Leu Ile Lys Ala Lys Lys
530                 535                 540
Gly Gly Lys Ser Lys Leu
545                 550
```

<210> SEQ ID NO 10
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 10

```
atggaagacg ccaaaaacat aaagaaaggc ccggcgccat tctatcctct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
```

```
cgagtcgtct taatgtatag atttgaagaa gagctgtttt tacgatccct tcaggattac    840
aaaattcaaa gtgcgttgct agtaccaacc ctatttttcat tcttcgccaa aagcactctg   900
attgacaaat acgatttatc taatttacac gaaattgctt ctgggggcgc acctctttcg   960
aaagaagtcg gggaagcggt tgcaaaacgc ttccatcttc cagggatacg acaaggatat  1020
gggctcactg agactacatc agctattctg attacacccg aggggatga taaaccgggc   1080 gcggtcggta agttgttcc attttttgaa gcgaaggttg tggatctgga taccgggaaa   1140
acgctgggcg ttaatcagag aggcgaatta tgtgtcagag gacctatgat tatgtccggt   1200
tatgtaaaca atccggaagc gaccaacgcc ttgattgaca aggatggatg ctacattct    1260 ggagacatag cttactggga cgaagacgaa cacttcttca tagttgaccg cttgaagtct  1320
ttaattaaat acaaaggata tcaggtggcc cccgctgaat tggaatcgat attgttacaa  1380
caccccaaca tccgtgacgc gggcgtggca ggtcttcccg acgatgacgc cggtgaactt  1440
cccgccgccg ttgttgtttt ggagcacgga aagacgatga cggaaaaaga gatcgtggat  1500
tacgtcgcca gtcaagtaac aaccgcgaaa aagttgcgcg gaggagttgt gtttgtggac  1560
gaagtaccga aaggtcttac cggaaaactc gacgcaagaa aaatcagaga gatcctcata  1620
aaggccaaga agggcggaaa gtccaaattg taa                                 1653
```

<210> SEQ ID NO 11
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 11

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205
```

```
Ala Leu Pro His Arg Thr Leu Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Lys Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 12
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 12
atggaagacg ccaaaaacat aaagaaaggc ccggcgccat tctatcctct agaggatgga    60
accgctggag agcaactgca taaggctatg aagagatacg ccctggttcc tggaacaatt   120
```

-continued

```
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccga agtcctttga tcgtgacaaa acaattgcac tgataatgaa ttcctctgga    600
tctactgggt tacctaaggg tgtggcctt ccgcatagaa ctttgtgcgt cagattctcg    660
catgccagag atcctatttt tggcaatcaa atcattccgg atactgcgat tttaagtgtt    720
gttccattcc atcacggttt tggaatgttt actacactcg gatatttgat atgtggattt    780
cgagtcgtct taatgtatag atttgaagaa gagctgtttt tacgatccct tcaggattac    840
aaaattcaaa gtgcgttgct agtaccaacc ctatttcat tcttcgccaa aagcactctg    900
attgacaaat acgatttatc taatttacac gaaattgctt ctgggggcgc acctcttcg    960 aaagaagtcg gggaagcggt tgcaaaacgc ttccatcttc cagggatacg acaaggatat    1020
gggctcactg agactacatc agctattctg attacaccca aggggatga taaaccgggc    1080 gcggtcggta agttgttcc attttttgaa gcgaaggttg tggatctgga taccgggaaa    1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380 cacccccaaca tcttcgacgc gggcgtggca ggtcttcccg acgatgacgc cggtgaactt    1440
cccgccgccg ttgttgtttt ggagcacgga agacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                  1653
```

<210> SEQ ID NO 13
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 13

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80
```

-continued

```
Cys Ser Glu Asn Ser Leu Gln Phe Phe Met Pro Val Leu Gly Ala Leu
             85                  90                  95
Phe Ile Gly Val Ala Val Ala Pro Ala Asn Asp Ile Tyr Asn Glu Arg
            100                 105                 110
Glu Leu Leu Asn Ser Met Asn Ile Ser Gln Pro Thr Val Val Phe Val
            115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
            195                 200                 205
Ala Leu Pro His Arg Thr Leu Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
            275                 280                 285
Pro Thr Leu Phe Ser Phe Phe Ala Lys Ser Thr Leu Ile Asp Lys Tyr
290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Lys Gly Asp Asp Lys Pro Gly Ala Val Gly Lys Val Val Pro Phe
            355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
            435                 440                 445
Val Ala Pro Ala Glu Leu Glu Ser Ile Leu Leu Gln His Pro Asn Ile
450                 455                 460
Arg Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
```

```
Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545             550

<210> SEQ ID NO 14
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 14
atggaagacg ccaaaaacat aaagaaaggc ccggcgccat tctatcctct agaggatgga      60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aagggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctttgtgcgt cagattctcg    660
catgccagag atcctatttt tggcaatcaa atcattccgg atactgcgat ttaagtgtt    720 gttccattcc atcacggttt tggaatgttt actacactcg atatttgat atgtggattt    780 cgagtcgtct taatgtatag atttgaagaa gagctgtttt tacgatccct tcaggattac    840
aaaattcaaa gtgcgttgct agtaccaacc ctattttcat tcttcgccaa aagcactctg    900
attgacaaat acgatttatc taatttacac gaaattgctt ctggggggcgc acctctttcg    960 aaagaagtcg ggaagcggt tgcaaaacgc ttccatcttc cagggatacg acaaggatat   1020
gggctcactg agactacatc agctattctg attacaccca aggggatga taaaccgggc   1080 gcggtcggta aagttgttcc attttttgaa gcgaaggttg tggatctgga taccgggaaa   1140
acgctgggcg ttaatcagag aggcgaatta tgtgtcagag acctatgat tatgtccggt   1200 tatgtaaaca atccggaagc gaccaacgcc ttgattgaca aggatggatg gctacattct   1260
ggagacatag cttactggga cgaagacgaa cacttcttca gttgaccg cttgaagtct   1320 ttaattaaat acaaaggata tcaggtggcc cccgctgaat tggaatcgat attgttacaa   1380
caccccaaca tccgtgacgc gggcgtggca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gtccaaattg taa                                1653
```

```
<210> SEQ ID NO 15
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 15

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Leu Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Arg Gly Asp Asp Lys Pro Gly Ala Val Gly Lys Val Val Pro Phe
        355                 360                 365
```

```
Phe Glu Ala Lys Val Val Asp Leu Asp Thr Gly Lys Thr Leu Gly Val
        370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp His Phe
        420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Arg Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 16
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 16
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aagggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggccctt ccgcatagaa ctttgtgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780 cgagtcgtct taatgtatag atttgaagaa gagctgtttt tacgatccct tcaggattac     840
aaaattcaaa gtgcgttgct agtaccaacc ctatttcat tcttcgccaa agcactctg     900 attgacaaat acgatttatc taatttacac gaaattgctt ctgggggcgc acctctttcg     960
```

```
aaagaagtcg gggaagcggt tgcaaaacgc ttccatcttc agggatacg acaaggatat   1020 gggctcactg agactacatc agctattctg attacacccc gtggggatga taaaccgggc   1080
gcggtcggta agttgttcc attttttgaa gcgaaggttg tggatctgga taccgggaaa   1140
acgctgggcg ttaatcagag aggcgaatta tgtgtcagag acctatgat tatgtccggt    1200 tatgtaaaca atccggaagc gaccaacgcc ttgattgaca aggatggatg ctacattct    1260 ggagacatag cttactggga cgaagacgaa cacttcttca tagttgaccg cttgaagtct   1320
ttaattaaat acaaaggata tcaggtggcc cccgctgaat tggaatcgat attgttacaa   1380 cacccccaaca tccgtgacgc gggcgtggca ggtcttcccg acgatgacgc cggtgaactt   1440
cccgccgccg ttgttgtttt ggagcacgga agacgatga cggaaaaaga gatcgtggat   1500
tacgtcgcca gtcaagtaac aaccgcgaaa aagttgcgcg gaggagttgt gtttgtggac   1560
gaagtaccga aggtcttac cggaaaactc gacgcaagaa aaatcagaga gatcctcata   1620
aaggccaaga agggcggaaa gtccaaattg taa                                1653
```

```
<210> SEQ ID NO 17
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 17

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Leu Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240
```

| | | | | | | | | | | |
|---|---|---|---|---|---|---|---|---|---|---|
|Val|Pro|Phe|His|His|Gly|Phe|Gly|Met|Phe|Thr|Thr|Leu|Gly|Tyr|Leu|
| | | | |245| | | |250| | | | |255| | |

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
        260                 265                 270

Phe Leu Arg Ser Leu Gln Asp Tyr Lys Ile Gln Ser Ala Leu Leu Val
    275                 280                 285

Pro Thr Leu Leu Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Lys Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
            420                 425                 430

Phe Ile Val Asp Arg Leu Lys Ser Leu Ile Lys Tyr Lys Gly Tyr Gln
    435                 440                 445

Val Ala Pro Ala Glu Leu Glu Ser Ile Leu Leu Gln His Pro Asn Ile
450                 455                 460

Arg Asp Ala Gly Val Ala Gly Leu Pro Asp Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Ile Lys Ala Lys Lys
    530                 535                 540

Gly Gly Lys Ser Lys Leu
545                 550

<210> SEQ ID NO 18
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 18
atggaagacg ccaaaaacat aaagaaaggc ccggcgccat tctatcctct agaggatgga    60
accgctggag agcaactgca taaggctatg aagagatacg ccctggttcc tggaacaatt   120
gcttttacag atgcacatat cgaggtgaac atcacgtacg cggaatactt cgaaatgtcc   180
gttcggttgg cagaagctat gaaacgatat gggctgaata caatcacag atcgtcgta   240 tgcagtgaaa actctcttca attctttatg ccggtgttgg gcgcgttatt tatcggagtt   300

```
gcagttgcgc ccgcgaacga catttataat gaacgtgaat tgctcaacag tatgaacatt    360
tcgcagccta ccgtagtgtt tgtttccaaa aaggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggcccct ccgcatagaa ctttgtgcgt cagattctcg    660
catgccagag atcctatttt tggcaatcaa atcattccgg atactgcgat tttaagtgtt    720
gttccattcc atcacggttt tggaatgttt actacactcg atatttgat atgtggattt    780 cgagtcgtct taatgtatag atttgaagaa gagctgtttt tacgatccct tcaggattac    840
aaaattcaaa gtgcgttgct agtaccaacc ctattgtcat tcttcgccaa aagcactctg    900
attgacaaat acgatttatc taatttacac gaaattgctt ctggggggcgc acctctttcg    960 aaagaagtcg gggaagcggt tgcaaaacgc ttccatcttc cagggatacg acaaggatat   1020
gggctcactg agactacatc agctattctg attacaccca aaggggatga taaaccgggc   1080
gcggtcggta agttgttcc attttttgaa gcgaaggttg tggatctgga taccgggaaa   1140
acgctgggcg ttaatcagag aggcgaatta tgtgtcagag acctatgat tatgtccggt   1200 tatgtaaaca atccggaagc gaccaacgcc ttgattgaca aggatggatg gctacattct   1260
ggagacatag cttactggga cgaagacgaa cacttcttca tagttgaccg cttgaagtct   1320
ttaattaaat acaaaggata tcaggtggcc cccgctgaat tggaatcgat attgttacaa   1380 cacccccaaca tccgtgacgc gggcgtggca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aggtcttac cggaaaactc gacgcaagaa aaatcagaga gatcctcata   1620
aaggccaaga agggcggaaa gtccaaattg taa                              1653
```

<210> SEQ ID NO 19
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 19

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110
```

```
Glu Leu Leu Asn Ser Met Asn Ile Ser Gln Pro Thr Val Val Phe Val
            115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
                180                 185                 190

Ala Leu Ile Met Asn Ser Ser Gly Ser Thr Gly Leu Pro Lys Gly Val
            195                 200                 205

Ala Leu Pro His Arg Thr Leu Cys Val Arg Phe Ser His Ala Arg Asp
            210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Leu Phe Ala Lys Ser Thr Leu Ile Asp Lys Tyr
            290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Lys Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
            370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Arg Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525
```

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 20
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 20
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct tccgcataga acttgtgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780 cgagtcgtct taatgtatag atttgaagaa gagctgtttt tacgatccct tcaggattac     840
aaaattcaaa gtgcgttgct agtaccaacc ctatttttcat tgttcgccaa agcactctg     900 attgacaaat acgatttatc taatttacac gaaattgctt ctgggggcgc acctctttcg     960
aaagaagtcg ggaagcggt tgcaaaacgc ttccatcttc cagggatacg acaaggatat    1020
gggctcactg agactacatc agctattctg attacaccca aggggatga taaaccgggc    1080 gcggtcggta agttgttcc attttttgaa gcgaaggttg tggatctgga taccgggaaa    1140
acgctgggcg ttaatcagag aggcgaatta tgtgtcagag acctatgat tatgtccggt    1200 tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tccgtgacgc gggcgtggca ggtcttcccg acgatgacgc cggtgaactt    1440
cccgccgccg ttgttgtttt ggagcacgga aagacgatga cggaaaaaga tcgtggat    1500 tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                1653

<210> SEQ ID NO 21
<211> LENGTH: 550
<212> TYPE: PRT
<213> ORGANISM: Artificial Sequence
<220> FEATURE:
<223> OTHER INFORMATION: Mutant firefly luciferase

<400> SEQUENCE: 21

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Leu Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Leu Ser Leu Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Lys Gly Asp Asp Lys Pro Gly Ala Val Gly Lys Val Val Pro Phe
        355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400
```

Tyr Val Asn Asn Pro Glu Ala Thr Asn Ala Leu Ile Asp Lys Asp Gly
            405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
            450                 455                 460

Arg Asp Ala Gly Val Ala Gly Leu Pro Asp Asp Asp Ala Gly Glu Leu
465                 470                 475                 480

Pro Ala Ala Val Val Leu Glu His Gly Lys Thr Met Thr Glu Lys
            485                 490                 495

Glu Ile Val Asp Tyr Val Ala Ser Gln Val Thr Thr Ala Lys Lys Leu
            500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 22
<211> LENGTH: 1653
<212> TYPE: DNA
<213> ORGANISM: Artificial Sequence
<220> FEATURE:
<223> OTHER INFORMATION: Mutant firefly luciferase

<400> SEQUENCE: 22
atggaagacg ccaaaaacat aaagaaaggc ccggcgccat tctatcctct agaggatgga     60
accgctggag agcaactgca taaggctatg aagagatacg ccctggttcc tggaacaatt    120
gcttttacag atgcacatat cgaggtgaac atcacgtacg cggaatactt cgaaatgtcc    180
gttcggttgg cagaagctat gaaacgatat gggctgaata caaatcacag aatcgtcgta    240
tgcagtgaaa actctcttca attctttatg ccggtgttgg gcgcgttatt tatcggagtt    300
gcagttgcgc ccgcgaacga catttataat gaacgtgaat tgctcaacag tatgaacatt    360
tcgcagccta ccgtagtgtt tgtttccaaa aagggggttgc aaaaaatttt gaacgtgcaa    420
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggcccct ccgcatagaa ctttgtgcgt cagattctcg    660
catgccagag atcctatttt tggcaatcaa atcattccgg atactgcgat tttaagtgtt    720
gttccattcc atcacggttt tggaatgttt actacactcg atatttgat atgtggattt    780 cgagtcgtct taatgtatag atttgaagaa gagctgtttt tacgatccct tcaggattac    840
aaaattcaaa gtgcgttgct agtaccaacc ctattgtcat tgttcgccaa aagcactctg    900
attgacaaat acgatttatc taatttacac gaaattgctt ctgggggcgc acctctttcg    960
aaagaagtcg ggaagcggt tgcaaaacgc ttccatcttc cagggatacg acaaggatat   1020
gggctcactg agactacatc agctattctg attacaccca agggggatga taaaccgggc   1080
gcggtcggta aagttgttcc attttttgaa gcgaaggttg tggatctgga taccgggaaa   1140

-continued

| | | | | |
|---|---|---|---|---|
| acgctgggcg | ttaatcagag | aggcgaatta | tgtgtcagag | gacctatgat | tatgtccggt | 1200 |
| tatgtaaaca | atccggaagc | gaccaacgcc | ttgattgaca | aggatggatg | gctacattct | 1260 |
| ggagacatag | cttactggga | cgaagacgaa | cacttcttca | tagttgaccg | cttgaagtct | 1320 |
| ttaattaaat | acaaaggata | tcaggtggcc | cccgctgaat | tggaatcgat | attgttacaa | 1380 |
| cacccaaca | tccgtgacgc | gggcgtggca | ggtcttcccg | acgatgacgc | cggtgaactt | 1440 |
| cccgccgccg | ttgttgtttt | ggagcacgga | aagacgatga | cggaaaaaga | gatcgtggat | 1500 |
| tacgtcgcca | gtcaagtaac | aaccgcgaaa | aagttgcgcg | gaggagttgt | gtttgtggac | 1560 |
| gaagtaccga | aaggtcttac | cggaaaactc | gacgcaagaa | aaatcagaga | gatcctcata | 1620 |
| aaggccaaga | agggcggaaa | gtccaaattg | taa | | | 1653 |

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ttgtgcgtca gattctcgca tgcca      25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
agttctatgc ggaagggcca caccc      25

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25 aaagggatg ataaaccggg cgcgg       25

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
gggtgtaatc agaatagctg atgtagtctc agtgagccc       39

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
cgtggggatg ataaaccggg cgc        23

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
gggtgtaatc agaatagctg atgtagtctc agtgagccc                    39

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
ttgtcattct tcgccaaaag cac                                     23

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
tagggttggt actagcaacg cact                                    24

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
ttgttcgcca aaagcactct gat                                     23

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
tgaaaatagg gttggtacta gcaacg                                  26

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
cgtgacgcgg gcgtggcagg tctt                                    24

<210> SEQ ID NO 34
<211> LENGTH: 31
<212> TYPE: DNA
<213> ORGANISM: Artificial Sequence
<220> FEATURE:
<223> OTHER INFORMATION: Primer

```
<400> SEQUENCE: 34
gatgttgggg tgttgtaaca atatcgattc c                                    31
```

HEAT-RESISTANT LUCIFERASE

CROSS-REFERENCE TO RELATED APPLICATION

This application is a 371 application of the international PCT application serial no. PCT/JP2018/010060, filed on Mar. 14, 2018, which claims the priority benefit of Japan application no. 2017-052502, filed on Mar. 17, 2017. The entirety of each of the abovementioned patent applications is hereby incorporated by reference herein and made a part of this specification.

TECHNICAL FIELD

The present invention relates to a thermostable luciferase.

BACKGROUND ART

Luciferases are enzymes that catalyze the chemical reaction in bioluminescence, as in luminescent bacteria and fireflies, which involves light emission by luminescent materials; luciferases are used as reporter enzymes in studies on gene expression and regulation in eukaryotic cells.

However, wild-type luciferases are only thermally stable at temperatures up to about 30° C. and their activity disappears at temperatures above 40° C. In addition to this lack of storage stability at high temperatures, luciferases have another problem in that they cannot be used in assays under high temperature reaction conditions that are intended for enhancing reaction rates.

In order to solve these problems, a variety of heat-resistant bacteria have been searched to discover thermostable luciferases (Patent Documents 1 to 6).

CITATION LIST

Patent Literature

Patent Document 1: Japanese Patent No. 5951325
Patent Document 2: Japanese Patent No. 3844082
Patent Document 3: Japanese Patent No. 3048466
Patent Document 4: Japanese Patent No. 3681911
Patent Document 5: Japanese Patent No. 5090304
Patent Document 6: Japanese Patent No. 5185479

SUMMARY OF INVENTION

Technical Problem

The present invention provides a new thermostable luciferase.

Solution to Problem

The present inventors have earnestly studied to solve these problems and, as a result, found that the thermal stability of a North American firefly luciferase is improved by mutating the amino acid residues at positions 292 and/or 294, thus completing the present invention.

The gist of the present invention is as follows:
(1) A mutant luciferase of the following (a) or (b):
(a) a mutant of a wild-type luciferase comprising the amino acid sequence of SEQ ID NO: 1, wherein phenylalanine at position 292 and/or phenylalanine at position 294 in the amino acid sequence of SEQ ID NO: 1 is substituted with another amino acid; or
(b) a mutant of a luciferase having 93% or more homology with the amino acid sequence of SEQ ID NO: 1, wherein in the amino acid sequence of the mutant, the amino acid at a site corresponding to position 292 and/or position 294 in the amino acid sequence of SEQ ID NO: 1 is substituted with another amino acid;
(2) The mutant luciferase according to (1), wherein the luciferase having 93% or more homology with the amino acid sequence of SEQ ID NO: 1 is such that at least one amino acid selected from the group consisting of alanine at position 215, glutamic acid at position 354, and phenylalanine at position 465 in the amino acid sequence of SEQ ID NO: 1 is substituted with another amino acid;
(3) A DNA encoding the mutant luciferase according to (1);
(4) A recombinant vector containing the DNA according to (3);
(5) A transformant containing the recombinant vector according to (4);
(6) A method for producing a mutant luciferase, comprising culturing the transformant according to (5);
(7) A kit comprising the mutant luciferase according to (1);
(8) A method for conducting bioluminescence assay using the mutant luciferase according to (1);
(9) The method according to (8), wherein the light emitted by a reaction between a target protein conjugated with the mutant luciferase according to (1) and a luminescent substrate is measured;
(10) The method according to (8), wherein the light emitted by a reaction between a luciferase reconstituted by association between a C-terminal fragment and an N-terminal fragment of the mutant luciferase according to (1) and a luminescent substrate is measured, the N-terminal fragment comprising position 292 in the amino acid sequence of SEQ ID NO: 1; and
(11) An N-terminal fragment of the mutant luciferase according to (1) for use in the method according to (10), the N-terminal fragment comprising position 292 in the amino acid sequence of SEQ ID NO: 1.

Advantageous Effects of Invention

According to the present invention, a new thermostable luciferase is provided.

The present application claims a priority to Japanese Patent Application No. 2017-52502, the contents in the description and/or drawings of which are incorporated herein.

BRIEF DESCRIPTION OF DRAWINGS

FIG. 1-2 shows the luminescent activity of a wild-type luciferase as compared with the luminescent activity of position-292 or position-294 mutant luciferase that remained after heat treatment.

FIG. 2 shows the luminescent activity of a wild-type luciferase introduced into a luminescent reagent as compared with the luminescent activities of similarly treated mutant luciferases that remained after warming (at 23° C.).

DESCRIPTION OF EMBODIMENTS

Figure 1:
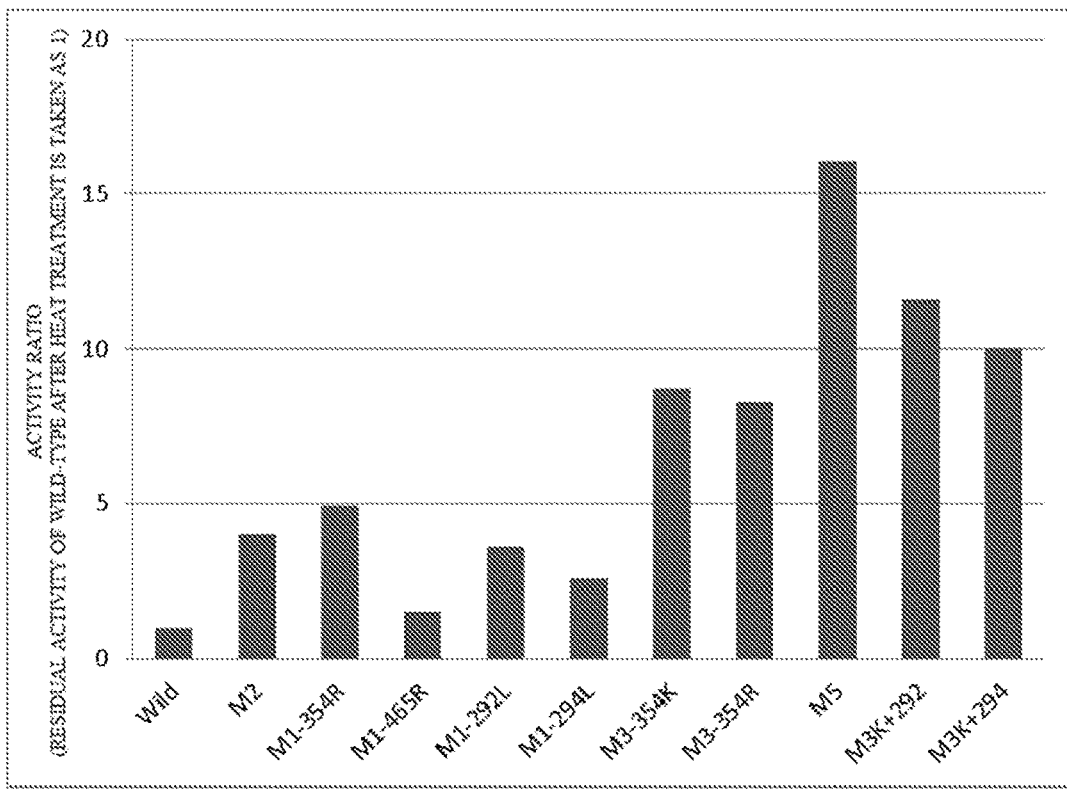
FIG. 1-1 shows the luminescent activity of a wild-type luciferase as compared with the luminescent activities of various mutant luciferases that remained after heat treatment.

The present invention will now be described in more detail by means of embodiments.

The present invention provides a mutant luciferase of the following (a) or (b):
(a) a mutant of a wild-type luciferase comprising the amino acid sequence of SEQ ID NO: 1, wherein phenylalanine at position 292 and/or phenylalanine at position 294 in the amino acid sequence of SEQ ID NO: 1 is substituted with another amino acid; or
(b) a mutant of a luciferase having 93% or more homology with the amino acid sequence of SEQ ID NO: 1, wherein in the amino acid sequence of the mutant, the amino acid at a site corresponding to position 292 and/or position 294 in the amino acid sequence of SEQ ID NO: 1 is substituted with another amino acid.

The luciferase mutant (a) is a mutant of a wild-type luciferase comprising the amino acid sequence of SEQ ID NO: 1. In this mutant, phenylalanine at position 292 and/or phenylalanine at position 294 in the amino acid sequence of SEQ ID NO: 1 is substituted with another amino acid. SEQ ID NO: 1 shows the amino acid sequence of a wild-type luciferase (North American firefly luciferase). Phenylalanine at position 292 and/or position 294 in the amino acid sequence of SEQ ID NO: 1 can be substituted with an amino acid other than phenylalanine. Examples of the amino acid other than phenylalanine include leucine, aliphatic amino acids other than leucine (glycine, alanine, valine, isoleucine, and methionine), aromatic amino acids (tryptophan, tyrosine, and thyroxine), hydrophobic amino acids such as proline, amide compounds having a carboxyl group and an amino group (glutamine and asparagine), acidic amino acids (glutamic acid and aspartic acid), and basic amino acids (lysine, arginine, and histidine). Among these amino acids, glycine, alanine, valine, leucine, isoleucine, methionine, glutamine, lysine, arginine, and histidine are preferred. Substituting an aromatic amino acid such as phenylalanine with an amino acid of another group, in particular, an aliphatic amino acid tends to provide a heat resisting effect. In addition, glycine, alanine, leucine, methionine, glutamine, glutamic acid, lysine, arginine, and histidine are considered to have a better chance of forming a three-dimensional structure similar to that of phenylalanine.

The luciferase mutant (b) is a mutant of a luciferase having 93% or more homology with the amino acid sequence of SEQ ID NO: 1. The luciferase having 93% or more homology with the amino acid sequence of SEQ ID NO: 1 may be naturally derived or mutated.

Examples of the luciferase include natural luciferases, for example, firefly natural luciferases (specifically, *Photinus pyralis* (North American firefly) natural luciferase, *Luciola lateralis* (Heike firefly)-derived luciferase, *Luciola cruciate* (Genji firefly)-derived luciferase, *Hotaria parvula* (Hime firefly)-derived luciferase, *Pynearinus termitilluminans*-derived luciferase, *Phrixothrix hirtus* (railroad worm)-derived luciferase, glow worm-derived luciferase, Cypridina-derived luciferase, and *Cavernularia obesa*-derived luciferase) and natural luciferases other than firefly luciferases (specifically, Dinoflagellate-derived luciferase, *Renilla*-derived luciferase, Kiyotake-derived luciferase, luminescent bacteria-derived luciferase, Rachia-derived luciferase, and luminescent lugworm-derived luciferase); and mutants thereof.

In the luciferase mutant (b), its amino acid sequence (having 93% or more homology with the amino acid sequence of SEQ ID NO: 1) is such that the amino acid at a site corresponding to position 292 and/or position 294 in the amino acid sequence of SEQ ID NO: 1 can be substituted with an amino acid other than phenylalanine. Examples of the amino acid other than phenylalanine include leucine, aliphatic amino acids other than leucine (glycine, alanine, valine, isoleucine, and methionine), aromatic amino acids (tryptophan, tyrosine, and thyroxine), hydrophobic amino acids such as proline, amide compounds having a carboxyl group and an amino group (glutamine and asparagine), acidic amino acids (glutamic acid and aspartic acid), basic amino acids (lysine, arginine, and histidine). Among these amino acids, glycine, alanine, valine, leucine, isoleucine, methionine, glutamine, lysine, arginine, and histidine are preferred. Substituting an aromatic amino acid such as phenylalanine with an amino acid of another group, in particular, an aliphatic amino acid tends to provide a heat resisting effect. In addition, it is inferred that glycine, alanine, leucine, methionine, glutamine, glutamic acid, lysine, arginine, and histidine are considered to have a better chance of forming a three-dimensional structure similar to that of phenylalanine.

The luciferase having 93% or more homology with the amino acid sequence of SEQ ID NO: 1 may have at least one amino acid substituted, deleted, and/or inserted in the amino acid sequence of SEQ ID NO: 1. The upper limit of the number of the substituted, deleted, and/or inserted amino acids can be 40, 30, 20, 10, 5, 4, 3, or 2.

The luciferase having 93% or more homology with the amino acid sequence of SEQ ID NO: 1 may be exemplified by a luciferase in which at least one amino acid selected from the group consisting of alanine at position 215, glutamic acid at position 354, and phenylalanine at position 465 in the amino acid sequence of SEQ ID NO: 1 is substituted with another amino acid. When alanine at position 215 in the amino acid sequence of SEQ ID NO: 1 is substituted with an amino acid other than alanine, the alanine can be substituted with, for example, an aliphatic amino acid (glycine, valine, leucine, isoleucine, or methionine), an aromatic amino acid (phenylalanine, tryptophan, tyrosine, or thyroxine), a hydrophobic amino acid such as proline, an amide compound having a carboxyl group and an amino group (glutamine or asparagine), an acidic amino acid (glutamic acid or aspartic acid), or a basic amino acid (lysine, arginine, or histidine). When glutamic acid at position 354 in the amino acid sequence of SEQ ID NO: 1 is substituted with an amino acid other than glutamic acid, the glutamic acid can be substituted with, for example, a positively charged amino acid such as lysine, arginine, or histidine, or a negatively charged amino acid such as aspartic acid. When phenylalanine at position 465 in the amino acid sequence of SEQ ID NO: 1 is substituted with an amino acid other than phenylalanine, the phenylalanine can be substituted with, for example, an aliphatic amino acid (glycine, alanine, valine, leucine, isoleucine, or methionine), an aromatic amino acid (tryptophan, tyrosine, or thyroxine), a hydrophobic amino acid such as proline, an amide compound having a carboxyl group and an amino group (glutamine or asparagine), an acidic amino acid (glutamic acid or aspartic acid), or a basic amino acid (lysine, arginine, or histidine).

Examples of the mutation in luciferase within the scope of the present invention include the following.
F292L
A215L, F292L
E354K (E354R), F292L F465R, F292L
A215L, E354K (E354R), F292L
A215L, F465R, F292L
E354K (E354R), F465R, F292L
A215L, E354K (E354R), F465R, F292L
F294L
A215L, F294L
E354K (E354R), F294L
F465R, F294L
A215L, E354K (E354R), F294L
A215L, F465R, F294L
E354K (E354R), F465R, F294L
A215L, E354K (E354R), F465R, F294L
F292L, F294L
A215L, F292L, F294L
E354K (E354R), F292L, F294L
F465R, F292L, F294L
A215L, E354K (E354R), F292L, F294L
A215L, F465R, F292L, F294L
E354K (E354R), F465R, F292L, F294L
A215L, E354K (E354R), F465R, F292L, F294L The mutant luciferase of the present invention is prepared by the following steps: inverse PCR is performed using a plasmid (template DNA) as a template having the DNA sequence of a wild-type luciferase incorporated into a vector and also using primers into which mutations have been introduced; the template plasmid is cleaved with restriction enzymes; thereafter, the PCR product as a linear plasmid is circularized by self-ligation to produce a mutant plasmid DNA; the plasmid is transformed in a host and cultured in a medium. This procedure can be performed using a KOD-plus mutagenesis kit (TOYOBO Co., Ltd.).

The DNA sequence of the wild-type luciferase comprising the amino acid sequence of SEQ ID NO: 1 is shown in SEQ ID NO: 2. The gene of the wild-type luciferase comprising the amino acid sequence of SEQ ID NO: 1 and a recombinant DNA of the gene can be prepared from North American firefly by a known method; alternatively, they can be purchased from Promega Corporation.

The present invention also provides a DNA encoding the mutant luciferase described above.

The present invention also provides a recombinant vector containing a DNA encoding the mutant luciferase described above. An expression vector into which the DNA encoding the mutant luciferase is to be incorporated may be commercially available, as exemplified by eukaryotic vectors including p3×FLAG-CMV-9, p3×FLAG-CMV-10, pXT1, pSG5, pSVK3, pBPV, pMSG, pSVL, and SV40, as well as bacterial vectors including pQE70, pQE60, pQE-9, pBluescript II KS, pTrc99a, pKK223-3, pDR540, pRIT2T, pET-11a, etc.

The expression vector may have added thereto a promoter, an enhancer, a splicing signal, a poly-A addition signal, a selection marker, or an SV40 replication origin, for example.

The recombinant vector containing a DNA encoding the mutant luciferase of the present invention may be introduced into a host to thereby obtain a transformant.

The host may be exemplified by bacterial cells (e.g., *Escherichia*, *Bacillus*, and *Bacillus subtilis* bacteria), fungal cells (e.g., yeasts and *Aspergillus* species), insect cells (e.g., S2 cells and Sf cells), animal cells (e.g., CHO cells, COS cells, HeLa cells, C127 cells, 3T3 cells, BHK cells, and HEK293 cells), plant cells, and so forth.

The recombinant vector may be transferred into a host either by the calcium phosphate method or by using instead a commercially available gene transfer reagent such as Lipofectamine or Lipofectamine 2000 (both are available from Invitrogen), GeneJuice (Merck), Xfect (Clontech Laboratories, Inc.), FuGENE 6 (Roche Applied Science), or HilyMax (Dojindo Laboratories).

The transformant can be cultured in a medium, and the mutant luciferase of the present invention can be collected from the culture. Accordingly, the present invention provides a method for producing a mutant luciferase which comprises culturing a transformant comprising a recombinant vector containing a DNA encoding the mutant luciferase. If the mutant luciferase is secreted in the medium, the medium is collected, and the mutant luciferase may be isolated from the medium and purified. If the mutant luciferase is generated in the transformed cells, the cells are lysed, and the mutant luciferase may be isolated from the lysate and purified.

The mutant luciferase of the present invention can be used in bioluminescence assay that utilizes a luciferase-luciferin reaction. Accordingly, the present invention provides a method for conducting bioluminescence assay using a mutant luciferase. In the bioluminescence assay, the light emitted by a reaction between a mutant luciferase-conjugated target protein and a luminescent substrate may be measured. The luminescent substrate may be a luciferin (for example, a multi-heteroorganic acid, D-(–)-2-(6'-hydroxy-2'-benzothiazolyl)-A2-thiazoline-4-carboxylic acid). The emission wavelength is appropriately set at 562 nm.

In order to perform the assay, the mutant luciferase of the present invention may constitute a kit together with an instruction manual, a luminescent substrate, and other reagents. Accordingly, the present invention also provides a kit comprising the mutant luciferase.

The bioluminescence assay method of the present invention may be a split-enzyme based assay, in which a luciferase reconstituted by association between a C-terminal fragment and an N-terminal fragment of the mutant luciferase is reacted with a luminescent substrate and the light emitted by the reaction is measured. The split-enzyme based assay of a luciferase is described in Japanese Patent No. 5816412, to which reference may be made. The present invention also provides a C-terminal or an N-terminal fragment of the mutant luciferase to be used in the split-enzyme based assay. The N-terminal fragment of the mutant luciferase may include an amino acid in the amino acid sequence of the mutant luciferase, where the amino acid is at position 292 in the amino acid sequence of SEQ ID NO: 1 or at a site corresponding thereto. The C-terminal fragment of the mutant luciferase may comprise a sequence consisting of sequential amino acids in the amino acid sequence of the mutant luciferase, where the sequence is at a site corresponding to positions 399 to 550 in the amino acid sequence of SEQ ID NO: 1, and the N-terminal fragment of the mutant luciferase may comprise a sequence consisting of sequential amino acids in the amino acid sequence of the mutant luciferase, where the sequence is at a site corresponding to positions 1 to 416 in the amino acid sequence of SEQ ID NO: 1. In each of the site corresponding to positions 399 to 550 and the site corresponding to positions 1 to 416, the first and the last amino acid may each vary in site by numbers of not more than about 17. In addition, the C-terminal fragment and the N-terminal fragment may include overlapping amino acid sequences. The number of such overlapping amino acids is preferably 1 to 200 and more preferably 5 to 30.

In the split-enzyme based assay, a fusion protein of a target protein and a C-terminal fragment of the mutant luciferase may be expressed in cells. For example, a DNA encoding the target protein and a DNA encoding the C-terminal fragment of the mutant luciferase are incorporated into an appropriate expression vector, which is transferred into appropriate cells, which are then cultured for an appropriate period of time to express the fusion protein in the cells. The DNA encoding the target protein and the DNA encoding the C-terminal fragment of the mutant luciferase can be prepared by a known method using, for example, PCR. The expression vector may be commercially available, as exemplified by eukaryotic vectors including p3×FLAG-CMV-9, p3×FLAG-CMV-10, pXT1, pSG5, pSVK3, pBPV, pMSG, pSVL, and SV40, as well as bacterial vectors including pQE70, pQE60, pQE-9, pBluescript II KS, pTrc99a, pKK223-3, pDR540, pRIT2T, pET-11a, and so forth. The DNA encoding the target protein may be incorporated either upstream or downstream of the DNA encoding the C-terminal fragment of the mutant luciferase. In addition, a linker sequence comprising 1 to 50 nucleotides may be inserted between the DNA encoding the target protein and the DNA encoding the C-terminal fragment of the mutant luciferase.

The cells expressing the fusion protein may be exemplified by bacterial cells (e.g., *Escherichia*, *Bacillus*, and *Bacillus subtilis* bacteria), fungal cells (e.g., yeasts and *Aspergillus* species), insect cells (e.g., S2 cells and Sf cells), animal cells (e.g., CHO cells, COS cells, HeLa cells, C127 cells, 3T3 cells, BHK cells, and HEK293 cells), plant cells, and so forth.

The expression vector into which a DNA encoding the target protein and a DNA encoding the C-terminal fragment of the mutant luciferase have been incorporated may be transferred into a host either by the calcium phosphate method or by using instead a commercially available gene transfer reagent such as Lipofectamine or Lipofectamine 2000 (both are available from Invitrogen), GeneJuice (Merck), Xfect (Clontech Laboratories, Inc.), FuGENE 6 (Roche Applied Science), or HilyMax (Dojindo Laboratories).

To obtain an N-terminal fragment of the mutant luciferase, a vector, for instance, into which a DNA encoding the N-terminal fragment of the mutant luciferase has been incorporated is transferred into a host for protein expression (e.g., *E. coli*), the host being then cultured for an appropriate period of time, and the protein of interest (the N-terminal fragment of the mutant luciferase) can be collected from the culture. In the case where the protein of interest is secreted in the medium, the latter is collected, from which the protein of interest may be isolated and purified. In the case the protein of interest is generated in the host cells, the latter are lysed and the protein of interest may be isolated from the lysate and purified.

After the fusion protein is expressed in cells, the N-terminal fragment of the mutant luciferase is added to the cells, and the presence or absence of light emission or a change in emission wavelength is detected. For example, the N-terminal fragment of the mutant luciferase may be added to a culture broth of cells that express the fusion protein, the broth being left to stand undisturbed for an appropriate period of time and, thereafter, the presence or absence of light emission or a change in emission wavelength is detected. In the case of adding the N-terminal fragment of the mutant luciferase after the fusion protein of the protein of interest and the C-terminal fragment of the mutant luciferase is expressed in cells, the presence or absence of light emission or a change in emission wavelength may be detected after a luminescent substrate (luciferin) is added. The emission wavelength is appropriately set at 562 nm.

EXAMPLES

The present invention will now be described in detail based on the following examples, to which the present invention is by no means limited.

Example 1

Production of Mutant Luciferase

A plasmid for producing a mutant luciferase was produced based on the inverse PCR method (Ochman H, Gerber A S, Hartl D L (1988), Genetic applications of an inverse polymerase chain reaction, Genetics, 120(3): 621-623) by applying site-specific mutagenesis to a plasmid (template DNA) having a wild-type (Wild) luciferase introduced into a pET28a or pET28b vector (manufactured by Merck).

For PCR reaction, a reaction solution of the following composition was prepared and the sequence of treatments at 95° C. for 2 minutes, at 98° C. for 10 seconds and at 68° C. for 7 minutes was repeated 10 times.

Template DNA pET28a (pET28b)-WildLuc (50 ng/µL): 0.5 µL
Primer 1 (10 µmol/µL): 0.5 µL
Primer 2 (10 µmol/µL): 0.5 µL
2 mM dNTP mixture (manufactured by TOYOBO Co., Ltd.): 2.5 µL
Polymerase (manufactured by TOYOBO Co., Ltd.): 0.5 µL
10× buffer solution: 2.5 µL
Sterilized water: 18 µL The nucleotide sequences of primers 1 and 2 are shown in Table 1.

The amplified PCR product was first subjected to Dpn I treatment to digest the template plasmid (template DNA including the sequence of a wild-type luciferase). Subsequently, the DNA that was not digested by the Dpn I treatment was circularized by self-ligation to produce a plasmid DNA of a mutant. This plasmid DNA was transformed in *E. coli* BL21 (DE3) whose cells were then seeded on an LB agar medium containing 50 µg/mL kanamycin and cultured overnight at 37° C. For nucleotide sequence verification, the generated colonies were liquid-cultured and the plasmid DNA was extracted. A mutant luciferase having multiple mutation sites was produced by designing primers that would have sequences corresponding to the respective mutant amino acids and by then performing the procedure described above.

According to the method described above, mutant luciferases M2 (A215L, E354K), M1-354R (E354R), M1-465R (F465R), M3-354K (A215L, E354K, F465R), M3-354R (A215L, E354R, F465R), M5 (A215L, E354K, F465R, F292L, F294L), M3K+292 (A215L, E354K, F465R, F292L), M3K+294 (A215L, E354K, F465R, F294L), M1-292L (F292L), and M1-294L (F294L) were produced.

TABLE 1

Sequences of oligonucleotides used in production of mutants

| Mutation site | Primer sequence (primers 1 and 2) |
|---|---|
| A215L | TTGTGCGTCAGATTCTCGCATGCCA (SEQ ID NO: 23) AGTTCTATGCGGAAGGGCCACACCC (SEQ ID NO: 24) |

TABLE 1-continued

Sequences of oligonucleotides used in production of mutants

| Mutation site | Primer sequence (primers 1 and 2) |
|---|---|
| E354K | AAAGGGGATGATAAACCGGGCGCGG (SEQ ID NO: 25)<br>GGGTGTAATCAGAATAGCTGATGTAGTCTCAGTGAGCCC (SEQ ID NO: 26) |
| E354R | CGTGGGGATGATAAACCGGGCGC (SEQ ID NO: 27)<br>GGGTGTAATCAGAATAGCTGATGTAGTCTCAGTGAGCCC (SEQ ID NO: 28) |
| F292L | TTGTCATTCTTCGCCAAAAGCAC (SEQ ID NO: 29)<br>TAGGGTTGGTACTAGCAACGCACT (SEQ ID NO: 30) |
| F294L | TTGTTCGCCAAAAGCACTCTGAT (SEQ ID NO: 31)<br>TGAAAATAGGGTTGGTACTAGCAACG (SEQ ID NO: 32) |
| F465R | CGTGACGCGGGCGTGGCAGGTCTT (SEQ ID NO: 33)<br>GATGTTGGGGTGTTGTAACAATATCGATTCC (SEQ ID NO: 34) |

Example 2

Evaluation of Thermal Stability of Mutant Luciferase

The thermal stability of each recombinant luciferase was evaluated by the following procedure. BL21 (DE3) cells having a mutant plasmid introduced thereinto were seeded on an LB agar medium containing 50 µg/mL of kanamycin and 0.5 mM IPTG and cultured overnight at 37° C. A single colony of the bacterial cells were then placed in 200 µL of a lysis buffer to extract a mutant luciferase. The composition of the buffer used for the bacteriolysis was as follows:

Tris buffer solution (pH: 6.8 to 8.0, final concentration: 0.1 to 100 mM),

Triton X-100 (final concentration: 0.001% to 10%), and

Lysozyme (final concentration: 0.1 to 20 mg/mL).

The lysate was heated at 35° C. to 45° C. for 30 minutes, and the luminescent activity was measured using "PicaGene Luminescence Kit PGL 100" (manufactured by TOYO B-Net Co., Ltd.). FIG. 1-1 shows the luminescent activities of various mutant luciferases after heat treatment. This graph demonstrates that the luciferase mutants of the present invention are about 1.5 to 16 times more thermally stable than the wild-type luciferase. In addition, it was demonstrated that the mutation sites of F292L and F294L provide further improvement in thermal stability, compared to the thermal stability improved by known mutation sites and combination thereof. In particular, the mutant "M5" luciferase mutated at both sites of F292L and F294L in combination with known mutation sites improved the thermal stability from about 9 times to about 16 times that of the wild-type luciferase. This result shows a synergistic effect of F292L and F294L in achieving an improvement of thermal stability of a wild-type luciferase.

Figures 1, 2:
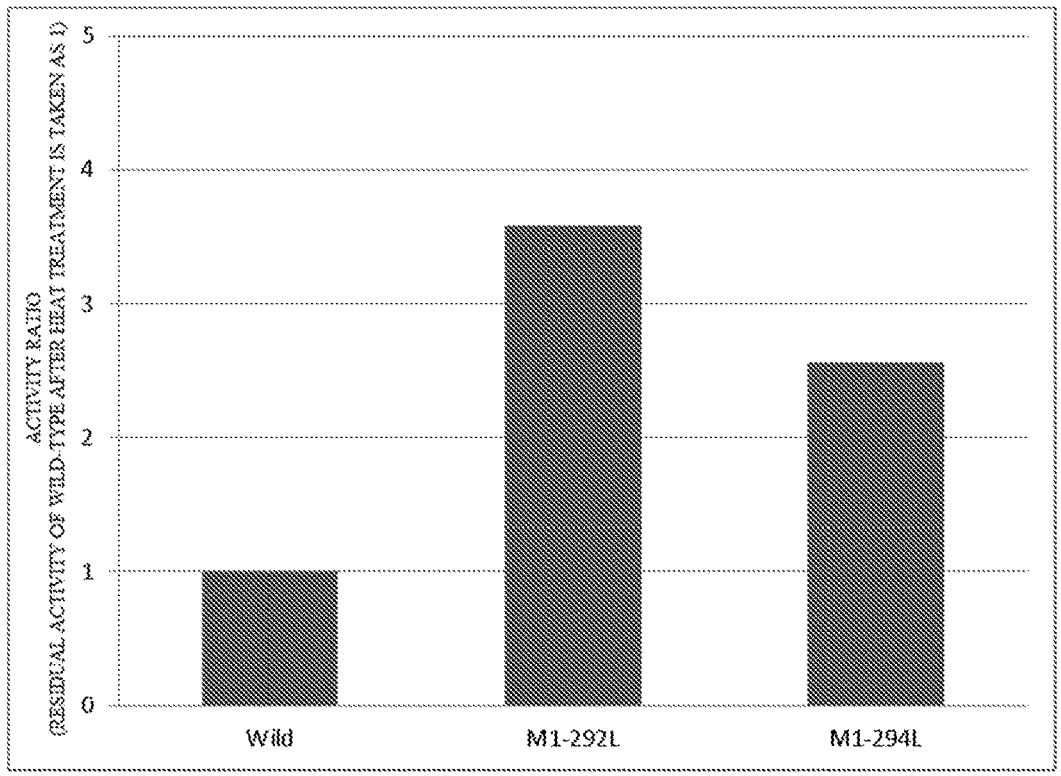
Figure 2:
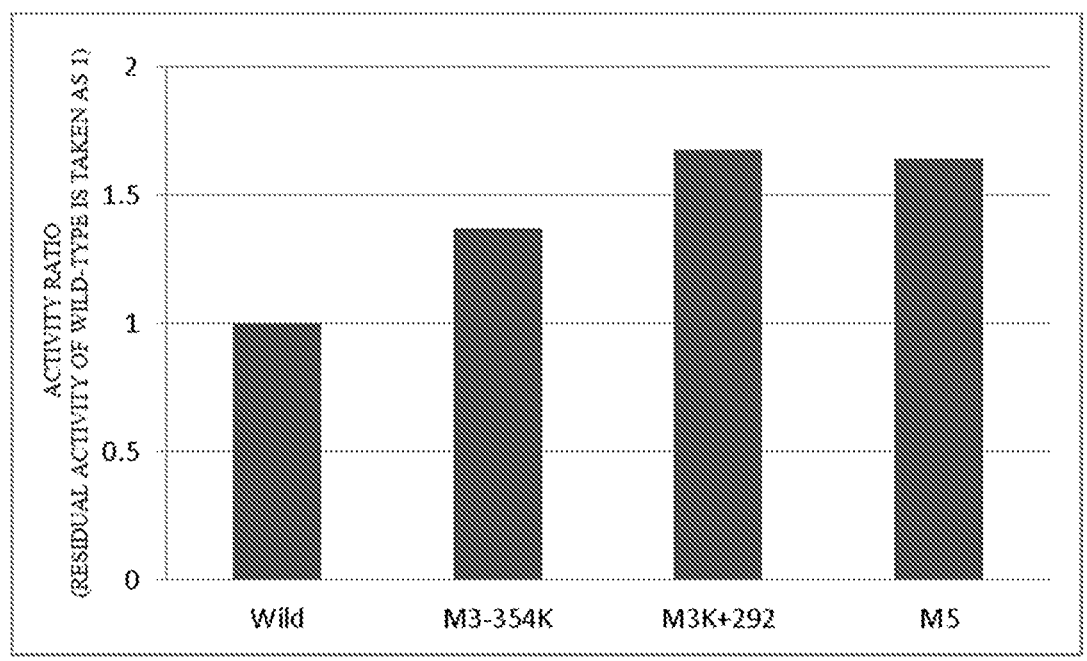

FIG. 1-2 shows a heat resisting effect as obtained by mutating position 292 or position 294 alone. The test was performed by the same method as used in FIG. 1-1, and the luminescent activity after heat treatment was compared with that of the wild type. This graph demonstrates that the mutations at positions 292 and 294 exhibit residual activities about 3.6 times and about 3.2 times, respectively, that of the wild type; it is therefore clear that thermal stability is provided even by single mutation.

Example 3

Evaluation of Thermal Stability as Attained when a Mutant Luciferase is Incorporated into a Luminescent Reagent E. coli BL21 (DE3) having any of the mutant luciferases incorporated thereinto was inoculated in an LB liquid medium containing 50 µg/mL of kanamycin and shake-cultured at 37° C. for several hours. At stages of OD600=0.3 to 0.7, IPTG (final concentration: 0.5 mM) was added to induce expression of each mutant luciferase, and the cells were harvested by centrifugation after culturing for about 5 hours. Total protein was extracted from the E. coli using the same lysis buffer as in Example 2. The mutant luciferase was purified from the extracted total protein using a His column bound with nickel.

Figure 3:
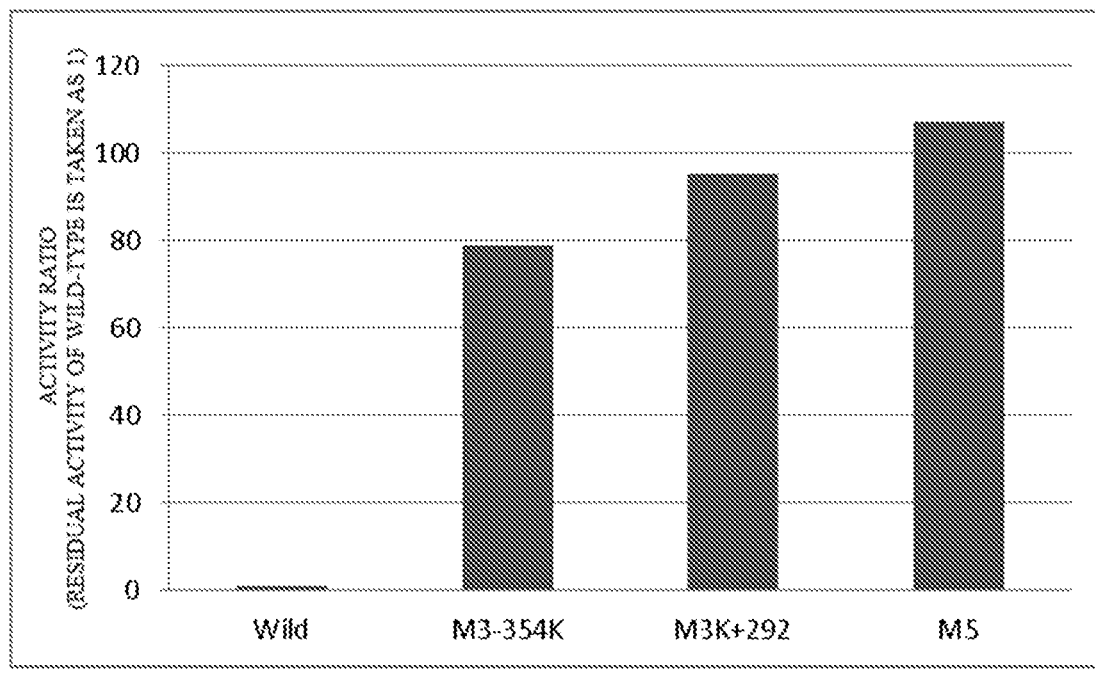
FIG. 3 shows the luminescent activity of a wild-type luciferase introduced into a luminescent reagent as compared with the luminescent activities of similarly treated mutant luciferases that remained after heating (at 40° C.).

Rather than the wild-type luciferase, the purified mutant luciferase was introduced into a luminescent reagent, "Cell" ATP Assay reagent (manufactured by TOYO B-Net Co., Ltd.) CA, and evaluated for thermal stability after it was introduced into the luminescent reagent. For evaluation of thermal stability, specifically, "stability at room temperature of 15° C. to 30° C." and "resistance to warming at 30° C. to 50° C.", treatment was performed by warming at 23° C. for 24 hours or heating at 40° C. for 30 minutes and the luminescent activities that remained after the treatments were measured. FIG. 2 shows data on the luminescent activity of the wild-type luciferase introduced into the luminescent reagent as compared with the luminescent activities of similarly treated mutant luciferases that remained after warming (at 23° C.). FIG. 3 shows data on the luminescent activity of the wild-type luciferase introduced into the luminescent reagent as compared with the luminescent activities of similarly treated mutant luciferases that remained after heating (at 40° C.). This graph demonstrates that the luciferase mutants of the present invention are about 1.6 to 107 times more thermally stable than the wild-type luciferase, even if they are present in a luminescent reagent. It is of particular note that the heat resisting effect was increased with an increase in temperature. In addition, it was demonstrated that as in Example 2, the mutation sites of F292L and F294L provide further improvement in thermal stability, compared to the thermal stability improved by known mutation sites and combination thereof.

Example 4

Measurement of Specific Activity of Mutant Luciferase

Figure 4:
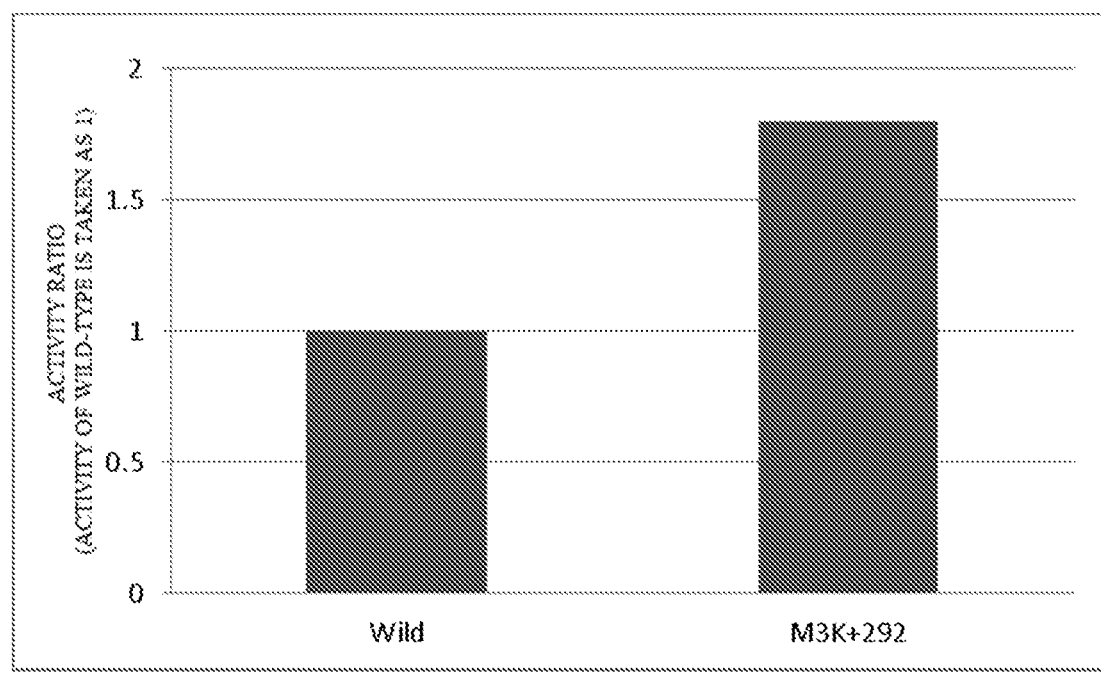
FIG. 4 shows a comparison of the activities of a wild-type luciferase and a mutant luciferase per unit mass of protein.

The specific activity per unit mass of protein was measured for one of the produced mutant luciferases and the wild-type luciferase. The specific activity was calculated using the amounts in which the respective luciferases were added to the luminescent reagent and the band intensities as numerically expressed after separation of the respective luciferases by SDS-PAGE. The results are shown in FIG. 4. It can be seen from this figure that a luciferase mutant of the present invention has a specific activity increased to about 1.8 times that of the wild-type luciferase, indicating a higher activity per unit mass of protein. This result means that luciferase used in the same unit mass of protein is detected as a higher amount of light emission; in other words, the luciferase-mediated light emission can be detected with an increased sensitivity.

All publications, patents, and patent applications cited in the present specification are incorporated in the specification in their entirety by reference.

INDUSTRIAL APPLICABILITY

The mutant luciferase of the present invention can be used in reporter assay, for example.

---

Sequence Listing Free Text

SEQ ID NO: 1: Amino acid sequence of wild-type luciferase
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTACVRFSHARDPIFGNQIIPDTAILSVVPFHHGFGMF
TTLGYLICGFRVVLMYRFEEELFLRSLQDYKIQSALLVPTLFSFFAKSTL
IDKYDLSNLHEIASGGAPLSKEVGEAVAKRFHLPGIRQGYGLTETTSAIL
ITPEGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIFDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 2: DNA sequence of wild-type luciferase
    1 atggaagacg ccaaaaacat aaagaaaggc ccggcgccat tctatcctct agaggatgga
   61 accgctggag agcaactgca taaggctatg aagagatacg ccctggttcc tggaacaatt
  121 gcttttacag atgcacatat cgaggtgaac atcacgtacg cggaatactt cgaaatgtcc
  181 gttcggttgg cagaagctat gaaacgatat gggctgaata caaatcacag aatcgtcgta
  241 tgcagtgaaa actctcttca attctttatg ccggtgttgg gcgcgttatt tatcggagtt
  301 gcagttgcgc ccgcgaacga catttataat gaacgtgaat tgctcaacag tatgaacatt
  361 tcgcagccta ccgtagtgtt tgtttccaaa aagggggttgc aaaaaatttt gaacgtgcaa
  421 aaaaaattac caataatcca gaaattatt atcatggatt ctaaaacgga ttaccaggga
  481 tttcagtcga tgtacacgtt cgtcacatct catctacctc ccggttttaa tgaatacgat
  541 tttgtaccag agtcctttga tcgtgacaaa acaattgcac tgataatgaa ttcctctgga
  601 tctactgggt tacctaaggg tgtggcccct ccgcatagaa ctgcctgcgt cagattctcg
  661 catgccagag atcctatttt tggcaatcaa atcattccgg atactgcgat tttaagtgtt
  721 gttccattcc atcacggttt tggaatgttt actacactcg gatatttgat atgtggattt
  781 cgagtcgtct taatgtatag atttgaagaa gagctgtttt tacgatccct tcaggattac
  841 aaaattcaaa gtgcgttgct agtaccaacc ctattttcat tcttcgccaa aagcactctg
  901 attgacaaat acgatttatc taatttacac gaaattgctt ctggggcgc acctctttcg
  961 aaagaagtcg gggaagcggt tgcaaaacgc ttccatcttc cagggatacg acaaggatat
 1021 gggctcactg agactacatc agctattctg attacacccg aggggatga taaaccgggc
 1081 gcggtcggta aagttgttcc attttttgaa gcgaaggttg tggatctgga taccgggaaa
 1141 acgctgggcg ttaatcagag aggcgaatta tgtgtcagag gacctatgat tatgtccggt
 1201 tatgtaaaca atccggaagc gaccaacgcc ttgattgaca aggatggatg gctacattct
 1261 ggagacatag cttactggga cgaagacgaa cacttcttca tagttgaccg cttgaagtct
 1321 ttaattaaat acaaaggata tcaggtggcc cccgctgaat tggaatcgat attgttacaa
 1381 caccccaaca tcttcgacgc gggcgtggca ggtcttcccg acgatgacgc cggtgaactt
 1441 cccgccgccg ttgttgtttt ggagcacgga aagacgatga cggaaaaaga gatcgtggat
 1501 tacgtcgcca gtcaagtaac aaccgcgaaa aagttgcgcg gaggagttgt gtttgtggac
 1561 gaagtaccga aaggtcttac cggaaaactc gacgcaagaa aaatcagaga gatcctcata
 1621 aaggccaaga agggcggaaa gtccaaattg taa SEQ ID NO: 3: Amino acid sequence of M1-292L
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTACVRFSHARDPIFGNQIIPDTAILSVVPFHHGFGMF
TTLGYLICGFRVVLMYRFEEELFLRSLQDYKIQSALLVPTL<u>L</u>SFFAKSTL
IDKYDLSNLHEIASGGAPLSKEVGEAVAKRFHLPGIRQGYGLTETTSAIL
ITPEGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIFDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 4: DNA sequence of M1-292L
    1 atggaagacg ccaaaaacat aaagaaaggc ccggcgccat tctatcctct agaggatgga
   61 accgctggag agcaactgca taaggctatg aagagatacg ccctggttcc tggaacaatt
  121 gcttttacag atgcacatat cgaggtgaac atcacgtacg cggaatactt cgaaatgtcc
  181 gttcggttgg cagaagctat gaaacgatat gggctgaata caaatcacag aatcgtcgta
  241 tgcagtgaaa actctcttca attctttatg ccggtgttgg gcgcgttatt tatcggagtt
  301 gcagttgcgc ccgcgaacga catttataat gaacgtgaat tgctcaacag tatgaacatt
  361 tcgcagccta ccgtagtgtt tgtttccaaa aagggggttgc aaaaaatttt gaacgtgcaa
  421 aaaaaattac caataatcca gaaattatt atcatggatt ctaaaacgga ttaccaggga
  481 tttcagtcga tgtacacgtt cgtcacatct catctacctc ccggttttaa tgaatacgat
  541 tttgtaccag agtcctttga tcgtgacaaa acaattgcac tgataatgaa ttcctctgga
  601 tctactgggt tacctaaggg tgtggcccct ccgcatagaa ctgcctgcgt cagattctcg

```
 661 catgccagag atcctatttt tggcaatcaa atcattccgg atactgcgat tttaagtgtt
 721 gttccattcc atcacggttt tggaatgttt actacactcg gatatttgat atgtggattt
 781 cgagtcgtct taatgtatag atttgaagaa gagctgtttt tacgatccct tcaggattac
 841 aaaattcaaa gtgcgttgct agtaccaacc ctattgtcat tcttcgccaa aagcactctg
 901 attgacaaat acgatttatc taatttacac gaaattgctt ctggggcgc acctctttcg
 961 aaagaagtcg gggaagcggt tgcaaaacgc ttccatcttc cagggatacg acaaggatat
1021 gggctcactg agactacatc agctattctg attacacccg aggggatga taaaccgggc
1081 gcggtcggta aagttgttcc atttttgaa gcgaaggttg tggatctgga taccgggaaa
1141 acgctgggcg ttaatcagag aggcgaatta tgtgtcagag acctatgat tatgtccggt
1201 tatgtaaaca atccggaagc gaccaacgcc ttgattgaca aggatggatg gctacattct
1261 ggagacatag cttactggga cgaagacgaa cacttcttca tagttgaccg cttgaagtct
1321 ttaattaaat acaaaggata tcaggtggcc cccgctgaat tggaatcgat attgttacaa
1381 caccccaaca tcttcgacgc gggcgtggca ggtcttcccg acgatgacgc cggtgaactt
1441 cccgccgccg ttgttgtttt ggagcacgga aagacgatga cggaaaaaga gatcgtggat
1501 tacgtcgcca gtcaagtaac aaccgcgaaa aagttgcgcg gaggagttgt gtttgtggac
1561 gaagtaccga aaggtcttac cggaaaactc gacgcaagaa aaatcagaga gatcctcata
1621 aaggccaaga agggcggaaa gtccaaattg taa SEQ ID NO: 5: Amino acid sequence of M1-294L
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTACVRFSHARDPIFGNQIIPDTAILSVVPFHHGFGMF
TTLGYLICGERVVLMYRFEEELFLRSLQDYKIQSALLVPTLFSLFAKSTL
IDKYDLSNLHEIASGGAPLSKEVGEAVAKRFHLPGIRQGYGLTETTSAIL
ITPEGDDKPGAVGKVVPFFEAKVVDLDTGKTLGVNQRGELCVRGPMIMSG
YVNNPEATNALIDKDGWLHSGDIAYWDEDEHFFIVDRLKSLINKYKGYQVA
PAELESILLQHPNIFDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 6: DNA sequence of M1-294L
   1 atggaagacg ccaaaaacat aaagaaaggc ccggcgccat tctatcctct agaggatgga
  61 accgctggag agcaactgca taaggctatg aagagatacg ccctggttcc tggaacaatt
 121 gcttttacag atgcacatat cgaggtgaac atcacgtacg cggaatactt cgaaatgtcc
 181 gttcggttgg cagaagctat gaaacgatat gggctgaata caatcacag aatcgtcgta
 241 tgcagtgaaa actctcttca attctttatg ccggtcgttgg gcgcgttatt tatcggagtt
 301 gcagttcgcg ccgcgaacga catttataat gaacgtgaat tgctcaacag tatgaacatt
 361 tcgcagccta ccgtagtgtt tgtttccaaa aaggggttgc aaaaaatttt gaacgtgcaa
 421 aaaaaattac caataatcca gaaaattatt atcatggatt ctaaaacgga ttaccaggga
 481 tttcagtcga tgtacacgtt cgtcacatct catctacctc ccggttttaa taacatgat
 541 tttgtaccag agtcctttga tcgtgacaaa acaattgcac tgataatgaa ttcctctgga
 601 tctactgggt tacctaaggg tgtggccctt ccgcataaga ctgcctgcgt cagattctcg
 661 catgccagag atcctatttt tggcaatcaa atcattccgg atactgcgat tttaagtgtt
 721 gttccattcc atcacggttt tggaatgttt actacactcg gatatttgat atgtggattt
 781 cgagtcgtct taatgtatag atttgaagaa gagctgtttt tacgatccct tcaggattac
 841 aaaattcaaa gtgcgttgct agtaccaacc ctatttcat tgttcgccaa aagcactctg
 901 attgacaaat acgatttatc taatttacac gaaattgctt ctggggcgc acctctttcg
 961 aaagaagtcg gggaagcggt tgcaaaacgc ttccatcttc cagggatacg acaaggatat
1021 gggctcactg agactacatc agctattctg attacacccg aggggatga taaaccgggc
1081 gcggtcggta aagttgttcc atttttgaa gcgaaggttg tggatctgga taccgggaaa
1141 acgctgggcg ttaatcagag aggcgaatta tgtgtcagag acctatgat tatgtccggt
1201 tatgtaaaca atccggaagc gaccaacgcc ttgattgaca aggatggatg gctacattct
1261 ggagacatag cttactggga cgaagacgaa cacttcttca tagttgaccg cttgaagtct
1321 ttaattaaat acaaaggata tcaggtggcc cccgctgaat tggaatcgat attgttacaa
1381 caccccaaca tcttcgacgc gggcgtggca ggtcttcccg acgatgacgc cggtgaactt
1441 cccgccgccg ttgttgtttt ggagcacgga aagacgatga cggaaaaaga gatcgtggat
1501 tacgtcgcca gtcaagtaac aaccgcgaaa aagttgcgcg gaggagttgt gtttgtggac
1561 gaagtaccga aaggtcttac cggaaaactc gacgcaagaa aaatcagaga gatcctcata
1621 aaggccaaga agggcggaaa gtccaaattg taa SEQ ID NO: 7: Amino acid sequence of M1-354R
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTACVRFSHARDPIFGNQIIPDTAILSVVPFHHGFGMF
TTLGYLICGERVVLMYRFEEELFLRSLQDYKIQSALLVPTLFSFFAKSTL
IDKYDLSNLHEIASGGAPLSKEVGEAVAKRFHLPGIRQGYGLTETTSAIL
ITPRGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIFDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 8: DNA sequence of M1-354R
   1 atggaagacg ccaaaaacat aaagaaaggc ccggcgccat tctatcctct agaggatgga
  61 accgctggag agcaactgca taaggctatg aagagatacg ccctggttcc tggaacaatt
```

```
121  gcttttacag atgcacatat cgaggtgaac atcacgtacg cggaatactt cgaaatgtcc
181  gttcggttgg cagaagctat gaaacgatat gggctgaata caaatcacag aatcgtcgta
241  tgcagtgaaa actctcttca attctttatg ccggtgttgg gcgcgttatt tatcggagtt
301  gcagttgcgc ccgcgaacga catttataat gaacgtgaat tgctcaacag tatgaacatt
361  tcgcagccta ccgtagtgtt tgtttccaaa aaggggttgc aaaaaatttt gaacgtgcaa
421  aaaaaattac caataatcca gaaaattatt atcatggatt ctaaaacgga ttaccaggga
481  tttcagtcga tgtacacgtt cgtcacatct catctacctc ccggttttaa tgaatacgat
541  tttgtaccag agtccttga tcgtgacaaa acaattgcac tgataatgaa ttcctctgga
601  tctactgggt tacctaaggg tgtggccctt ccgcatagaa ctgcctgcgt cagattctcg
661  catgccagag atcctatttt tggcaatcaa atcattccgg atactgcgat tttaagtgtt
721  gttccattcc atcacggttt tggaatgttt actacactcg gatatttgat atgtggattt
781  cgagtcgtct taatgtatag atttgaagaa gagctgtttt tacgatccct tcaggattac
841  aaaattcaaa gtgcgttgct agtaccaacc ctattttcat tcttcgccaa aagcactctg
901  attgacaaat acgatttatc taatttacac gaattgctt ctggggggcgc acctctttcg
961  aaagaagtcg gggaagcggt tgcaaaacgc ttccatcttc cagggatacg acaaggatat
1021 gggctcactg agactacatc agctattctg attacacccc gtggggatga taaaccgggc
1081 gcggtcggta aagttgttcc attttttgaa gcgaaggttg tggatctgga tacccgggaaa
1141 acgctgggcg ttaatcagag aggcgaatta tgtgtcagag acctatgat tatgtccggt
1201 tatgtaaaca atccggaagc gaccaacgcc ttgattgaca aggatggatg gctacattct
1261 ggagacatag cttactggga cgaagacgaa cacttcttca tagttgaccg cttgaagtct
1321 ttaattaaat acaaaggata tcaggtggcc cccgctgaat tggaatcgat attgttacaa
1381 cacccccaaca tcttcgacgc gggcgtggca ggtcttcccg acgatgacgc cggtgaactt
1441 cccgccgccg ttgttgtttt ggagcacgga aagacgatga cggaaaaaga gatcgtggat
1501 tacgtcgcca gtcaagtaac aaccgcgaaa aagttgcgcg gaggagttgt gtttgtggac
1561 gaagtaccga aaggtcttac cggaaaactc gacgcaagaa aaatcagaga gatcctcata
1621 aaggccaaga agggcggaaa gtccaaattg taa SEQ ID NO: 9: Amino acid sequence of M1-465R
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTACVRFSHARDPIFGNQIIPDTAILSVVPFHHGFGMF
TTLGYLICGERVVLMYRFEEELFLRSLQDYKIQSALLVPTLFSFFAKSTL
IDKYDLSNLHEIASGGAPLSKEVGEAVAKRFHLPGIRQGYGLTETTSAIL
ITPEGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIRDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 10: DNA sequence of M1-465R
  1  atggaagacg ccaaaaacat aaagaaaggc ccggcgccat tctatcctct agaggatgga
 61  accgctgag agcaactgca taaggctatg aagagatacg ccctggttcc tggaacaatt
121  gcttttacag atgcacatat cgaggtgaac atcacgtacg cggaatactt cgaaatgtcc
181  gttcggttgg cagaagctat gaaacgatat gggctgaata caaatcacag aatcgtcgta
241  tgcagtgaaa actctcttca attctttatg ccggtgttgg gcgcgttatt tatcggagtt
301  gcagttgcgc ccgcgaacga catttataat gaacgtgaat tgctcaacag tatgaacatt
361  tcgcagccta ccgtagtgtt tgtttccaaa aaggggttgc aaaaaatttt gaacgtgcaa
421  aaaaaattac caataatcca gaaaattatt atcatggatt ctaaaacgga ttaccaggga
481  tttcagtcga tgtacacgtt cgtcacatct catctacctc ccggttttaa tgaatacgat
541  tttgtaccag agtcctttga tcgtgacaaa acaattgcac tgataatgaa ttcctctgga
601  tctactgggt tacctaaggg tgtggccctt ccgcatagaa ctgcctgcgt cagattctcg
661  catgccagag atcctatttt tggcaatcaa atcattccgg atactgcgat tttaagtgtt
721  gttccattcc atcacggttt tggaatgttt actacactcg gatatttgat atgtggattt
781  cgagtcgtct taatgtatag atttgaagaa gagctgtttt tacgatccct tcaggattac
841  aaaattcaaa gtgcgttgct agtaccaacc ctattttcat tcttcgccaa aagcactctg
901  attgacaaat acgatttatc taatttacac gaattgcttt ctggggggcgc acctctttcg
961  aaagaagtcg gggaagcggt tgcaaaacgc ttccatcttc cagggatacg acaaggatat
1021 gggctcactg agactacatc agctattctg attacacccg aggggggatga taaaccgggc
1081 gcggtcggta aagttgttcc attttttgaa gcgaaggttg tggatctgga tacccgggaaa
1141 acgctgggcg ttaatcagag aggcgaatta tgtgtcagag acctatgat tatgtccggt
1201 tatgtaaaca atccggaagc gaccaacgcc ttgattgaca aggatggatg gctacattct
1261 ggagacatag cttactggga cgaagacgaa cacttcttca tagttgaccg cttgaagtct
1321 ttaattaaat acaaaggata tcaggtggcc cccgctgaat tggaatcgat attgttacaa
1381 cacccccaaca tccgtgacgc gggcgtggca ggtcttcccg acgatgacgc cggtgaactt
1441 cccgccgccg ttgttgtttt ggagcacgga aagacgatga cggaaaaaga gatcgtggat
1501 tacgtcgcca gtcaagtaac aaccgcgaaa aagttgcgcg gaggagttgt gtttgtggac
1561 gaagtaccga aaggtcttac cggaaaactc gacgcaagaa aaatcagaga gatcctcata
1621 aaggccaaga agggcggaaa gtccaaattg taa SEQ ID NO: 11: Amino acid sequence of M2
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTLCVRFSHARDPIFGNQIIPDTAILSVVPFHHGFGMF
TTLGYLICGFRVVLMYRFEEELFLRSLQDYKIQSALLVPTLFSFFAKSTL
```

```
IDKYDLSNLHEIASGGAPLSKEVGEAVAKRFHLPGIRQGYGLTETTSAIL
ITPKGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIFDAGVAGLPDDDAGELPAAVVVLEHGKTMTEKEIVD
YVASQVTTAKKLRGGVVFVDEVPKGLTGKLDARKIREILIKAKKGGKSKL

SEQ ID NO: 12: DNA sequence of M2
    1 atggaagacg ccaaaaacat aaagaaaggc ccggcgccat tctatcctct agaggatgga
   61 accgctggag agcaactgca taaggctatg aagagatacg ccctggttcc tggaacaatt
  121 gcttttacag atgcacatat cgaggtgaac atcacgtacg cggaatactt cgaaatgtcc
  181 gttcggttgg cagaagctat gaaacgatat gggctgaata caaatcacag aatcgtcgta
  241 tgcagtgaaa actctcttca attctttatg ccggtgttgg gcgcgttatt tatcggagtt
  301 gcagttgcgc ccgcgaacga catttataat gaacgtgaat tgctcaacag tatgaacatt
  361 tcgcagccta ccgtagtgtt tgtttccaaa aaggggttgc aaaaaatttt gaacgtgcaa
  421 aaaaaattac caataatcca gaaaattatt atcatggatt ctaaaacgga ttaccaggga
  481 tttcagtcga tgtacacgtt cgtcacatct catctacctc ccggttttaa tgaatacgat
  541 tttgtaccag agtcctttga tcgtgacaaa acaattgcac tgataatgaa ttcctctgga
  601 tctactgggt tacctaaggg tgtggccctt ccgcatagaa ctttgtgcgt cagattctcg
  661 catgccagag atcctatttt tggcaatcaa atcattccgg atactgcgat tttaagtgtt
  721 gttccattcc atcacggttt ggaatgttt actacactcg gatatttgat atgtggattt
  781 cgagtcgtct aatgtatag atttgaagaa gagctgtttt tacgatccct tcaggattac
  841 aaaattcaaa gtgcgttgct agtaccaacc ctattttcat tcttcgccaa aagcactctg
  901 attgacaaat acgatttatc taatttacac gaaattgctt ctggggcgc acctctttcg
  961 aaagaagtcg gggaagcggt tgcaaaacgc ttccatcttc cagggatacg acaaggatat
 1021 gggctcactg agactacatc agctattctg attacaccca aaggggatga taaaccgggc
 1081 gcggtcggta agttgttcc atttttgaa gcgaaggttg gatctgga taccgggaaa
 1141 acgctgggcg ttaatcagag aggcgaatta tgtgtcagag acctatgat tatgtccggt
 1201 tatgtaaaca atccggaagc gaccaacgcc ttgattgaca aggatggatg gctacattct
 1261 ggagacatag cttactggga cgaagacgaa cacttcttca tagttgaccg cttgaagtct
 1321 ttaattaaat acaaaggata tcaggtggcc ccgctgaat tggaatcgat attgttacaa
 1381 caccccaaca tcttcgacgc gggcgtggca ggtctcccg acgatgacgc cggtgaactt
 1441 cccgccgcg ttgttgtttt ggagcacgga aagacgatga cggaaaaaga gatcgtggat
 1501 tacgtcgcca gtcaagtaac aaccgcgaaa aagttgcgcg gaggagttgt gtttgtggac
 1561 gaagtaccga aaggtcttac cggaaaactc gacgcaagaa aaatcagaga gatcctcata
 1621 aaggccaaga agggcggaaa gtccaaattg taa SEQ ID NO: 13: Amino acid sequence of M3-354K
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTLCVRFSHARDPIFGNQIIPDTAILSVVPFHHGFGMF
TTLGYLICGERVVLMYRFEEELFLRSLQDYKIQSALLVPTLFSFFAKSTL
IDKYDLSNLHEIASGGAPLSKEVGEAVAKRFHLPGIRQGYGLTETTSAIL
ITPKGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIRDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 14: DNA sequence of M3-354K
    1 atggaagacg ccaaaaacat aaagaaaggc ccggcgccat tctatcctct agaggatgga
   61 accgctggag agcaactgca taaggctatg aagagatacg ccctggttcc tggaacaatt
  121 gcttttacag atgcacatat cgaggtgaac atcacgtacg cggaatactt cgaaatgtcc
  181 gttcggttgg cagaagctat gaaacgatat gggctgaata caaatcacag aatcgtcgta
  241 tgcagtgaaa actctcttca attctttatg ccggtgttgg gcgcgttatt tatcggagtt
  301 gcagttgcgc ccgcgaacga catttataat gaacgtgaat tgctcaacag tatgaacatt
  361 tcgcagccta ccgtagtgtt tgtttccaaa aaggggttgc aaaaaatttt gaacgtgcaa
  421 aaaaaattac caataatcca gaaaattatt atcatggatt ctaaaacgga ttaccaggga
  481 tttcagtcga tgtacacgtt cgtcacatct catctacctc ccggttttaa tgaatacgat
  541 tttgtaccag agtcctttga tcgtgacaaa acaattgcac tgataatgaa ttcctctgga
  601 tctactgggt tacctaaggg tgtggccctt ccgcatagaa ctttgtgcgt cagattctcg
  661 catgccagag atcctatttt tggcaatcaa atcattccgg atactgcgat tttaagtgtt
  721 gttccattcc atcacggttt ggaatgttt actacactcg gatatttgat atgtggattt
  781 cgagtcgtct aatgtatag atttgaagaa gagctgtttt tacgatccct tcaggattac
  841 aaaattcaaa gtgcgttgct agtaccaacc ctattttcat tcttcgccaa aagcactctg
  901 attgacaaat acgatttatc taatttacac gaaattgctt ctggggcgc acctctttcg
  961 aaagaagtcg gggaagcggt tgcaaaacgc ttccatcttc cagggatacg acaaggatat
 1021 gggctcactg agactacatc agctattctg attacaccca aaggggatga taaaccgggc
 1081 gcggtcggta agttgttcc atttttgaa gcgaaggttg gatctgga taccgggaaa
 1141 acgctgggcg ttaatcagag aggcgaatta tgtgtcagag acctatgat tatgtccggt
 1201 tatgtaaaca atccggaagc gaccaacgcc ttgattgaca aggatggatg gctacattct
 1261 ggagacatag cttactggga cgaagacgaa cacttcttca tagttgaccg cttgaagtct
 1321 ttaattaaat acaaaggata tcaggtggcc ccgctgaat tggaatcgat attgttacaa
 1381 caccccaaca tccgtgacgc gggcgtggca ggtctcccg acgatgacgc cggtgaactt
 1441 cccgccgcg ttgttgtttt ggagcacgga aagacgatga cggaaaaaga gatcgtggat
 1501 tacgtcgcca gtcaagtaac aaccgcgaaa aagttgcgcg gaggagttgt gtttgtggac
```

```
1561 gaagtaccga aaggtcttac cggaaaactc gacgcaagaa aaatcagaga gatcctcata
1621 aaggccaaga agggcggaaa gtccaaattg taa
```

SEQ ID NO: 15: Amino acid sequence of M3-354R
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRT<u>L</u>CVRFSHARDPIFGNQIIPDTAILSVVPFHHGFGMF
TTLGYLICGERVVLMYRFEEELFLRSLQDYKIQSALLVPTLFSFFAKSTL
IDKYDLSNLHEIASGGAPLSKEVGEAVAKRFHLPGIRQGYGLTETTSAIL
ITPRGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIRDAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 16: DNA sequence of M3-354R
```
   1 atggaagacg ccaaaaacat aaagaaaggc ccggcgccat tctatcctct agaggatgga
  61 accgctggag agcaactgca taaggctatg aagagatacg ccctggttcc tggaacaatt
 121 gcttttacag atgcacatat cgaggtgaac atcacgtacg cggaatactt cgaaatgtcc
 181 gttcggttgg cagaagctat gaaacgatat gggctgaata caaatcacag aatcgtcgta
 241 tgcagtgaaa actctcttca attctttatg ccggtgttgg gcgcgttatt tatcggagtt
 301 gcagttgcgc ccgcgaacga catttataat gaacgtgaat tgctcaacag tatgaacatt
 361 tcgcagccta ccgtagtgtt tgtttccaaa aaggggttgc aaaaaatttt gaacgtgcaa
 421 aaaaaattac caataatcca gaaaattatt atcatggatt ctaaaacgga ttaccaggga
 481 tttcagtcga tgtacacgtt cgtcacatct catctacctc ccggttttaa tgaatacgat
 541 tttgtaccag agtcctttga tcgtgacaaa acaattgcac tgataatgaa ttcctctgga
 601 tctactgggt tacctaaggg tgtggccctt ccgcatagaa ct<u>ttg</u>tgcgt cagattctcg
 661 catgccagag atcctatttt tggcaatcaa atcattccgg atactgcgat tttaagtgtt
 721 gttccattcc atcacggttt tggaatgttt actacactcg gatatttgat atgtggattt
 781 cgagtcgtct taatgtatag atttgaagaa gagctgtttt tacgatccct tcaggattac
 841 aaaattcaaa gtgcgttgct agtaccaacc ctatttttca tcttcgccaa aagcactctg
 901 attgacaaat acgatttatc taatttacac gaaattgctt ctggggggcgc acctctttcg
 961 aaagaagtcg gggaagcggt tgcaaaacgc ttccatcttc agggatacg acaaggatat
1021 gggctcactg agactacatc agctattctg attacacc<u>cc gt</u>ggggatga taaaccgggc
1081 gcggtcggta aagttgttcc atttttttgaa gcgaaggttg tggatctgga tacggggaaa
1141 acgctgggcg ttaatcagag aggcgaatta tgtgtcagag gacctatgat tatgtccggt
1201 tatgtaaaca atccggaagc gaccaacgcc ttgattgaca aggatggatg gctacattct
1261 ggagacatag cttactggga cgaagacgaa cacttcttca gagttgaccg cttgaagtct
1321 ttaattaaat acaaaggata tcaggtggcc cccgctgaat tggaatcgat attgttacaa
1381 caccccaaca tc<u>cgt</u>gacgc gggcgtggca ggtcttccgg acgatgacgc cggtgaactt
1441 cccgccgccg ttgttgtttt ggagcacgga aagacgatga cggaaaaaga gatcgttgat
1501 tacgtcgcca gtcaagtaac aaccgcgaaa aagttgcgcg gagagttgt gtttgtggac
1561 gaagtaccga aaggtcttac cggaaaactc gacgcaagaa aaatcagaga gatcctcata
1621 aaggccaaga agggcggaaa gtccaaattg taa
```

SEQ ID NO: 17: Amino acid sequence of M3K + 292
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRT<u>L</u>CVRFSHARDPIFGNQIIPDTAILSVVPFHHGFGMF
TTLGYLICGFRVVLMYRFEEELFLRSLQDYKIQSALLVPTLSFFAKSTL
IDKYDLSNLHEIASGGAPLSKEVGEAVAKRFHLPGIRQGYGLTETTSAIL
ITPKGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNI<u>R</u>DAGVAGLPDDDAGELPAAVVVLEHGKTMTEKEIVD
YVASQVTTAKKLRGGVVFVDEVPKGLTGKLDARKIREILIKAKKGGKSKL SEQ ID NO: 18: IM1A sequence of M3K + 292
```
   1 atggaagacg ccaaaaacat aaagaaaggc ccggcgccat tctatcctct agaggatgga
  61 accgctggag agcaactgca taaggctatg aagagatacg ccctggttcc tggaacaatt
 121 gcttttacag atgcacatat cgaggtgaac atcacgtacg cggaatactt cgaaatgtcc
 181 gttcggttgg cagaagctat gaaacgatat gggctgaata caaatcacag aatcgtcgta
 241 tgcagtgaaa actctcttca attctttatg ccggtgttgg gcgcgttatt tatcggagtt
 301 gcagttgcgc ccgcgaacga catttataat gaacgtgaat tgctcaacag tatgaacatt
 361 tcgcagccta ccgtagtgtt tgtttccaaa aaggggttgc aaaaaatttt gaacgtgcaa
 421 aaaaaattac caataatcca gaaaattatt atcatggatt ctaaaacgga ttaccaggga
 481 tttcagtcga tgtacacgtt cgtcacatct catctacctc ccggttttaa tgaatacgat
 541 tttgtaccag agtcctttga tcgtgacaaa acaattgcac tgataatgaa ttcctctgga
 601 tctactgggt tacctaaggg tgtggccctt ccgcatagaa ct<u>ttg</u>tgcgt cagattctcg
 661 catgccagag atcctatttt tggcaatcaa atcattccgg atactgcgat tttaagtgtt
 721 gttccattcc atcacggttt tggaatgttt actacactcg gatatttgat atgtggattt
 781 cgagtcgtct taatgtatag atttgaagaa gagctgtttt tacgatccct tcaggattac
 841 aaaattcaaa gtgcgttgct agtaccaacc ct<u>attg</u>tcat tcttcgccaa aagcactctg
 901 attgacaaat acgatttatc taatttacac gaaattgctt ctggggggcgc acctctttcg
 961 aaagaagtcg gggaagcggt tgcaaaacgc ttccatcttc agggatacg acaaggatat
```

```
1021  gggctcactg agactacatc agctattctg attacaccca aaggggatga taaaccgggc
1081  gcggtcggta aagttgttcc attttttgaa gcgaaggttg tggatctgga tacccggaaa
1141  acgctgggcg ttaatcagag aggcgaatta tgtgtcagag gacctatgat tatgtccggt
1201  tatgtaaaca atccggaagc gaccaacgcc ttgattgaca aggatggatg gctacattct
1261  ggagacatag cttactggga cgaagacgaa cacttcttca tagttgaccg cttgaagtct
1321  ttaattaaat acaaaggata tcaggtggcc cccgctgaat tggaatcgat attgttacaa
1381  caccccaaca tccgtgacgc gggcgtggca ggtcttcccg acgatgacgc cggtgaactt
1441  cccgccgccg ttgttgtttt ggagcacgga aagacgatga cggaaaaaga gatcgtggat
1501  tacgtcgcca gtcaagtaac aaccgcgaaa aagttgcgcg gaggagttgt gtttgtggac
1561  gaagtaccga aaggtcttac cggaaaaactc gacgcaagaa aaatcagaga gatcctcata
1621  aaggccaaga agggcggaaa gtccaaattg taa
```

SEQ ID NO: 19: Amino acid sequence of M3K + 294
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTLCVRFSHARDPIFGNQIIPDTAILSVVPFHHGFGMF
TTLGYLICGERVVLMYRFEEELFLRSLQDYKIQSALLVPTLFSLFAKSTL
IDKYDLSNLHEIASGGAPLSKEVGEAVAKRFHLPGIRQGYGLTETTSAIL
ITPKGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIRDAGVAGLPDDDAGELPAAVVVLEHGKTMTEKEIVD
YVASQVTTAKKLRGGVVFVDEVPKGLTGKLDARKIREILIKAKKGGKSKL

```
SEQ ID NO: 20: DNA sequence of M3K + 294
    1  atggaagacg ccaaaaacat aaagaaaggc ccggcgccat tctatcctct agaggatgga
   61  accgctggag agcaactgca taaggctatg aagagatacg ccctggttcc tggaacaatt
  121  gcttttacag atgcacatat cgaggtgaac atcacgtacg cggaatactt cgaaatgtcc
  181  gttcggttgg cagaagctat gaaacgatat gggctgaata caaatcacag aatcgtcgta
  241  tgcagtgaaa actctcttca attctttatg ccggtgttgg gcgcgttatt tatcggagtt
  301  gcagttgcgc ccgcgaacga catttataat gaacgtgaat tgctcaacag tatgaacatt
  361  tcgcagccta ccgtagtgtt tgtttccaaa aaggggttgc aaaaaatttt gaacgtgcaa
  421  aaaaaattac caataatcca gaaaattatt atcatggatt ctaaaacgga ttaccaggga
  481  tttcagtcga tgtacacgtt cgtcacatct catctacctc ccggttttaa tgaatacgat
  541  tttgtaccag agtcctttga tcgtgacaaa acaattgcac tgataatgaa ttcctctgga
  601  tctactgggt tacctaaggg tgtggccctt ccgcatagaa ctttgtgcgt cagattctcg
  661  catgccagag atccatttg tggcaatcaa atcattccgg atactgcgat tttaagtgtt
  721  gttccattcc atcacggttt tggaatgttt actacactcg gatatttgat atgtggattt
  781  cgagtcgtct taatgtatag atttgaagaa gagctgtttt tacgatccct tcaggattac
  841  aaaattcaaa gtgcgttgct agtaccaacc ctatttttct gttcgccaa aagcactctg
  901  attgacaaat acgatttatc taatttacac gaaattgctt ctgggggcgc acctctttcg
  961  aaagaagtcg ggaagcggt tgcaaaacgc ttccatcttc caggggatacg acaaggatat
 1021  gggctcactg agactacatc agctattctg attacaccca aaggggatga taaaccgggc
 1081  gcggtcggta aagttgttcc attttttgaa gcgaaggttg tggatctgga tacccggaaa
 1141  acgctgggcg ttaatcagag aggcgaatta tgtgtcagag gacctatgat tatgtccggt
 1201  tatgtaaaca atccggaagc gaccaacgcc ttgattgaca aggatggatg gctacattct
 1261  ggagacatag cttactggga cgaagacgaa cacttcttca tagttgaccg cttgaagtct
 1321  ttaattaaat acaaaggata tcaggtggcc cccgctgaat tggaatcgat attgttacaa
 1381  caccccaaca tccgtgacgc gggcgtggca ggtcttcccg acgatgacgc cggtgaactt
 1441  cccgccgccg ttgttgtttt ggagcacgga aagacgatga cggaaaaaga gatcgtggat
 1501  tacgtcgcca gtcaagtaac aaccgcgaaa aagttgcgcg gaggagttgt gtttgtggac
 1561  gaagtaccga aaggtcttac cggaaaaactc gacgcaagaa aaatcagaga gatcctcata
 1621  aaggccaaga agggcggaaa gtccaaattg taa
```

SEQ ID NO: 21: Amino acid sequence of MS
MEDAKNIKKGPAPFYPLEDGTAGEQLHKAMKRYALVPGTIAFTDAHIEVN
ITYAEYFEMSVRLAEAMKRYGLNTNHRIVVCSENSLQFFMPVLGALFIGV
AVAPANDIYNERELLNSMNISQPTVVFVSKKGLQKILNVQKKLPIIQKII
IMDSKTDYQGFQSMYTFVTSHLPPGFNEYDFVPESFDRDKTIALIMNSSG
STGLPKGVALPHRTLCVRFSHARDPIFGNQIIPDTAILSVVPFHHGFGMF
TTLGYLICGERVVLMYRFEEELFLRSLQDYKIQSALLVPTLLSLFAKSTL
IDKYDLSNLHEIASGGAPLSKEVGEAVAKRFHLPGIRQGYGLTETTSAIL
ITPKGDDKPGAVGKVVPFFEAKVVDLDTGKTLGVNQRGELCVRGPMIMSG
YVNNPEATNALIDKDGWLHSGDIAYWDEDEHFFIVDRLKSLIKYKGYQVA
PAELESILLQHPNIRDAGVAGLPDDDAGELPAAVVVLEHGKTMTEKEIVD
YVASQVTTAKKLRGGVVFVDEVPKGLTGKLDARKIREILIKAKKGGKSKL

```
SEQ ID NO: 22: DNA sequence of MS
    1  atggaagacg ccaaaaacat aaagaaaggc ccggcgccat tctatcctct agaggatgga
   61  accgctggag agcaactgca taaggctatg aagagatacg ccctggttcc tggaacaatt
  121  gcttttacag atgcacatat cgaggtgaac atcacgtacg cggaatactt cgaaatgtcc
  181  gttcggttgg cagaagctat gaaacgatat gggctgaata caaatcacag aatcgtcgta
  241  tgcagtgaaa actctcttca attctttatg ccggtgttgg gcgcgttatt tatcggagtt
  301  gcagttgcgc ccgcgaacga catttataat gaacgtgaat tgctcaacag tatgaacatt
  361  tcgcagccta ccgtagtgtt tgtttccaaa aaggggttgc aaaaaatttt gaacgtgcaa
  421  aaaaaattac caataatcca gaaaattatt atcatggatt ctaaaacgga ttaccaggga
```

```
 481 tttcagtcga tgtacacgtt cgtcacatct catctaccte ccggttttaa tgaatacgat
 541 tttgtaccag agtcctttga tcgtgacaaa acaattgcac tgataatgaa ttcctctgga
 601 tctactgggt tacctaaggg tgtggccctt ccgcatagaa ctttgtgcgt cagattctcg
 661 catgccagag atcctatttt tggcaatcaa atcattccgg atactgcgat tttaagtgtt
 721 gttccattcc atcacggttt tggaatgttt actacactcg gatatttgat atgtggattt
 781 cgagtcgtct taatgtatag atttgaagaa gagctgtttt tacgatccct tcaggattac
 841 aaaattcaaa gtgcgttgct agtaccaacc ctattgtcat tgttcgccaa aagcactctg
 901 attgacaaat acgatttatc taatttacac gaaattgctt ctgggggcgc acctctttcg
 961 aaagaagtcg ggaagcggtt gcaaaacgc ttccatcttc cagggatacg acaaggatat
1021 gggctcactg agactacatc agctattctg attacaccca aaggggatga taaaccgggc
1081 gcggtcggta agttgttcc attttttgaa gcgaaggttg tggatctgga taccgggaaa
1141 acgctgggcg ttaatcagag aggcgaatta tgtgtcagag gacctatgat tatgtccggt
1201 tatgtaaaca atccggaagc gaccaacgcc ttgattgaca aggatggatg gctacattct
1261 ggagacatag cttactggga cgaagacgaa cacttcttca tagttgaccg cttgaagtct
1321 ttaattaaat acaaaggata tcaggtggcc cccgctgaat tggaatcgat attgttacaa
1381 caccccaaca tccgtgacgc gggcgttggc ggtcttcccg acgatgacgc cggtgaactt
1441 cccgccgccg ttgttgtttt ggagcacgga aagacgatga cggaaaaaga gatcgtggat
1501 tacgtcgcca gtcaagtaac aaccgcgaaa aagttgcgcg gaggagttgt gtttgtggac
1561 gaagtaccga aaggtcttac cggaaaactc gacgcaagaa aaatcagaga gatcctcata
1621 aaggccaaga agggcggaaa gtccaaattg taa
```

SEQ ID NO: 23: DNA sequence of primer sequence (primer 1) for mutation site A215L
TTGTGCGTCAGATTCTCGCATGCCA SEQ ID NO: 24: DNA sequence of primer sequence (primer 2) for mutation site A215L
AGTTCTATGCGGAAGGGCCACACCC SEQ ID NO: 25: DNA sequence of primer sequence (primer 1) for mutation site E354K
AAAGGGGATGATAAACCGGGCGCGG SEQ ID NO: 26: DNA sequence of primer sequence (primer 2) for mutation site E354K
GGGTGTAATCAGAATAGCTGATGTAGTCTCAGTGAGCCC SEQ ID NO: 27: DNA sequence of primer sequence (primer 1) for mutation site E354R
CGTGGGGATGATAAACCGGGCGC SEQ ID NO: 28: DNA sequence of primer sequence (primer 2) for mutation site E354R
GGGTGTAATCAGAATAGCTGATGTAGTCTCAGTGAGCCC SEQ ID NO: 29: DNA sequence of primer sequence (primer 1) for mutation site F292L
TTGTCATTCTTCGCCAAAAGCAC SEQ ID NO: 30: DNA sequence of primer sequence (primer 2) for mutation site F292L
TAGGGTTGGTACTAGCAACGCACT SEQ ID NO: 31: DNA sequence of primer sequence (primer 1) for mutation site F294L
TTGTTCGCCAAAAGCACTCTGAT SEQ ID NO: 32: DNA sequence of primer sequence (primer 2) for mutation site F294L
TGAAAATAGGGTTGGTACTAGCAACG SEQ ID NO: 33: DNA sequence of primer sequence (primer 1) for mutation site F465R
CGTGACGCGGGCGTGGCAGGTCTT SEQ ID NO: 34: DNA sequence of primer sequence (primer 2) for mutation site F465R
GATGTTGGGGTGTTGTAACAATATCGATTCC

The invention claimed is:

1. A thermostable luciferase of the following (a) or (b):
   (a) a luciferase comprising the amino acid sequence of SEQ ID NO: 1, wherein phenylalanine at position 292 in the amino acid sequence of SEQ ID NO: 1 is substituted with glycine, alanine, valine, leucine, isoleucine, methionine, glutamine, glutamic acid, lysine, arginine, or histidine, or wherein phenylalanine at position 292 and phenylalanine at position 294 in the amino acid sequence of SEQ ID NO: 1 are substituted with glycine, alanine, valine, leucine, isoleucine, methionine, glutamine, glutamic acid, lysine, arginine, or histidine; or
   (b) a luciferase having 93% or more sequence identity to the amino acid sequence of SEQ ID NO: 1 with the exception of the amino acid corresponding to residue at position 292 has the substitution of glycine, alanine, valine, leucine, isoleucine, methionine, glutamine, glutamic acid, lysine, arginine, or histidine or with the exception of the amino acid corresponding to residue at position 292 and position 294 have the substitution of glycine, alanine, valine, leucine, isoleucine, methionine, glutamine, glutamic acid, lysine, arginine, or histidine,
   wherein said thermostable luciferase has increased thermostability as compared to a wild-type luciferase.

2. The thermostable luciferase of claim 1, wherein the luciferase having 93% or more sequence identity to the amino acid sequence of SEQ ID NO: 1 further comprises at least one substitution at an amino acid residue selected from the group consisting of alanine corresponding to position 215, glutamic acid corresponding to position 354, and phenylalanine corresponding to position 215, glutamic acid corresponding to position 465 in the amino acid sequence of SEQ ID NO: 1.

3. A kit comprising the thermostable luciferase according to of claim 1.

4. A method for conducting a bioluminescence assay comprising:
   providing the thermostable luciferase of claim 1 conjugated with a target protein;
   measuring a light emitted by a reaction between said thermostable luciferase conjugated with a target protein and a luminescent substrate.

5. An N-terminal fragment of a thermostable luciferase of the following (a) or (b)
   (a) a luciferase comprising the amino acid sequence of SEQ ID NO: 1, wherein phenylalanine at position 292 in the amino acid sequence of SEQ ID NO: 1 is substituted with glycine, alanine, valine, leucine, isoleucine, methionine, glutamine, glutamic acid, lysine, arginine, or histidine, or wherein phenylalanine at position 292 and phenylalanine at position 294 in the amino acid sequence of SEQ ID NO: 1 are substituted with glycine, alanine, valine, leucine, isoleucine, methionine, glutamine, glutamic acid, lysine, arginine, or histidine; or
   (b) a luciferase having 93% or more sequence identity to the amino acid sequence of SEQ ID NO: 1 with the exception of the amino acid corresponding to residue at position 292 has the substitution of glycine, alanine, valine, leucine, isoleucine, methionine, glutamine, glutamic acid, lysine, arginine, or histidine or with the exception of the amino acid corresponding to residue at position 292 and position 294 have the substitution of glycine, alanine, valine, leucine, isoleucine, methionine, glutamine, glutamic acid, lysine, arginine, or histidine,
   wherein the N-terminal fragment comprises position 292 of the amino acid sequence of SEQ ID NO: 1, and wherein said thermostable luciferase has increased thermostability as compared to a wild-type luciferase.

* * * * *